(12) United States Patent
Liu

(10) Patent No.: US 9,534,257 B2
(45) Date of Patent: Jan. 3, 2017

(54) MULTIPLEX NUCLEIC ACID DETECTION METHODS AND SYSTEMS

(71) Applicant: Timothy Z. Liu, Fremont, CA (US)

(72) Inventor: Timothy Z. Liu, Fremont, CA (US)

(73) Assignee: LIFEOS GENOMICS CORPORATION, Grand Cayman (KY)

( * ) Notice: Subject to any disclaimer, the term of this patent is extended or adjusted under 35 U.S.C. 154(b) by 229 days.

(21) Appl. No.: 14/099,827

(22) Filed: Dec. 6, 2013

(65) Prior Publication Data

US 2014/0093876 A1 Apr. 3, 2014

Related U.S. Application Data

(60) Division of application No. 13/252,095, filed on Oct. 3, 2011, now Pat. No. 8,603,743, which is a continuation of application No. PCT/US2010/029777, filed on Apr. 2, 2010.

(60) Provisional application No. 61/166,479, filed on Apr. 3, 2009, provisional application No. 61/166,553, filed on Apr. 3, 2009, provisional application No. 61/172,660, filed on Apr. 24, 2009, provisional application No. 61/266,037, filed on Dec. 2, 2009.

(51) Int. Cl.
C12Q 1/68 (2006.01)
C07H 21/00 (2006.01)

(52) U.S. Cl.
CPC .......... *C12Q 1/6886* (2013.01); *C12Q 1/6844* (2013.01)

(58) Field of Classification Search
CPC ......... C12Q 1/68; C12Q 1/686; C12Q 1/6869; C07H 21/00; C07H 21/04; C12P 19/34
See application file for complete search history.

(56) References Cited

U.S. PATENT DOCUMENTS

| | | |
|---|---|---|
| 4,988,617 A | 1/1991 | Landegren et al. |
| 5,474,796 A | 12/1995 | Brennan |
| 5,604,097 A | 2/1997 | Brenner |
| 5,679,524 A | 10/1997 | Nikiforov et al. |
| 5,846,719 A | 12/1998 | Brenner et al. |
| 5,985,551 A | 11/1999 | Brennan |
| 6,130,073 A | 10/2000 | Eggerding |
| 6,143,496 A | 11/2000 | Brown et al. |
| 6,287,778 B1 | 9/2001 | Huang et al. |
| 6,544,738 B2 | 4/2003 | Wold |
| 6,607,878 B2 | 8/2003 | Sorge |
| 6,638,722 B2 | 10/2003 | Ji et al. |
| 7,323,305 B2 | 1/2008 | Leamon et al. |
| 2003/0008285 A1 | 1/2003 | Fischer |
| 2005/0074774 A1 | 4/2005 | Woudenberg et al. |
| 2008/0153135 A1 | 6/2008 | Liu |
| 2008/0268440 A1 | 10/2008 | Liu et al. |
| 2009/0035825 A1 | 2/2009 | Kotler et al. |
| 2009/0062129 A1 | 3/2009 | McKernan et al. |
| 2009/0143234 A1 | 6/2009 | Palaniappan |
| 2009/0318298 A1 | 12/2009 | Kim et al. |

FOREIGN PATENT DOCUMENTS

| | | |
|---|---|---|
| WO | 99/37819 A2 | 7/1999 |
| WO | 0056927 A2 | 9/2000 |
| WO | 2005029041 A2 | 3/2005 |
| WO | 2007121489 A2 | 10/2007 |

OTHER PUBLICATIONS

Pandey et al., Ch. 3 : Applied Biosystems SOLiD System : Ligation based Sequencing. in Next-Generation Genome Sequencing : Towards Personalized Medicine Edited by Michal Janitz (2008).*
Shendure et al., Next-generation DNA Sequencing. Nature Biotechnology 26 (10) :1135 (2008).*
Vogelstein et al., Digital PCR, Proc. Natl. Acad. Sci. USA, 1999, vol. 96, pp. 9236-9241.
Pohl et al., Principle and applications of digital PCR, Expert Rev. Mol. Diagn, 2004, 4(1):41-47.
Diehl et al., Digital quantification of mutant DNA in cancer patients, Curr Opin Oncol, 2007, 19:36-42.
Dressman et al., Transforming single DNA molecules into fluorescent magnetic particles for detection and enumeration of genetic variations, PNAS, 2003, 100(15):8817-8822.
Weisenberger et al., DNA methylation analysis by digital bisulfite genomic sequencing and digital MethyLight, Nucleic Acids Res., 2008, 36(14):4689-4698.
Diehl et al., Detection and quantification of mutations in the plasma of patients with colorectal tumors, PNAS, 2005, 102(45):16368-16373.
Diehl et al., Analysis of Mutations in DNA Isolated From Plasma and Stool of Colorectal Cancer Patients, Gastroenterol., 2008, 135(2):489-498.
Lo et al., Digital PCR for the molecular detection of fetal chromosomal aneuploidy, PNAS, 2007, 104 (32):13116-13121.
Dube et al., Mathematical Analysis of Copy Number Variation in a DNA Sample Using Digital PCR on a Nanofluidic Device, PLoS One, 2008,3(8),e2876.
Warren et al. The Digital Array Response Curve, Mar. 8, 2007, retrieved from Stanford University website thebigone.stanford.edu/quake/publications/DigResCurve.pdf.
Eriksson et al., Multiplex and quantifiable detection of nucleic acid from pathogenic fungi using padlock probes, generic real time PCR and specific suspension array readout, J. Microbiol. Methods, 2009, 78, 195-202.
Baner et al., Signal amplification of padlock probes by rolling circle replication, Nucl. Acids Res., 1998, 26 (22):5073-5078.
Baner et al., More keys to padlock probes: mechanisms for high-throughput nucleic acid analysis, Curr. Opinion Biotech., 2001, 12, 11-15.
Drmanac et al., Human Genome Sequencing Using Unchained Base Reads on Self-Assembling DNA Nanoarrays, Science, 2010, 327:78-81.

(Continued)

*Primary Examiner* — Ethan C Whisenant
(74) *Attorney, Agent, or Firm* — Knobbe Martens Olson & Bear LLP

(57) ABSTRACT

The present invention relates to methods and systems for single molecule based nucleic acid amplification and subsequent detection of nucleic acid molecules, and particularly to the determination of SNPs, mutations, and to the diagnosis of diseases associated with the changes of these nucleic acid molecules.

17 Claims, 12 Drawing Sheets

(56) References Cited

OTHER PUBLICATIONS

Li et al., Multiplex co-amplification of 24 retinoblastoma gene exons after pre-amplification by long-distance PCR, Nucleic Acids Res., 1996, 24(3):538-539.

Mengual et al., Multiplex preamplification of specific cDNA targets prior to gene expression analysis by TaqMan Arrays, BMC Research Notes, 2008, 1:21.

Xia et al., Simultaneous quantitative assessment of circulating cell-free mitochondrial and nuclear DNA by multiplex real-time PCR, Genet. & Mol. Biol., 2009: 32 (1), 20-24.

Arneson et al., Whole-Genome Amplification by Improved Primer Extension Preamplification PCR (I-PEP-PCR), Cold Spring Harb. Protoc., 2008, 5 pages.

Gerry et al., Universal DNA Microarray Method for Multiplex Detection of Low Abindance Point Mutations, J. Mol. Biol., 1999, vol. 292, 251-262.

Luo et al., Improving the fidelity of Thermus thermophilus DNA ligase, Nucleic Acids Res., 1996, 24(14):3071-3078.

Odell et al., Footprinting of Chlorella Virus DNA Ligase Bound at a Nick in Duplex DNA*, The Jour. of Biol. Chem., 1999, 274(20):14032-14039.

Blow, N., PCR's next frontier, Nature Methods, 2007, 4(10):869-875.

Phillips et al., Evaluation of the Genplex SNP typing system and a 49plex forensic marker panel, Forensic Sci. Intl.: Genetics 2007, 1(2) 180-185.

Cheung et al., Whole genome amplifications using a degenerate oligonucleotide primer allows hundreds of genotypes to be performed on less than one nanogram of enomic DNA, PNAS 93: 14676 (1996).

Grossman et al., High-density multiplex detection of nucleic acid sequences: oligonucleotide ligation assay and sequence-coded separation. Nucleic Acids Research 22 (21): 4527 (1994).

Sanchez et al., A multiplex assay with 52 single nucleotide polymorphisms for human identification. Electrophoresis 27: 1713 (2006).

\* cited by examiner

Table 1. Color codes of paired-probe ligation

| 3'-LISP \ 5'-LISP | A-L1 | C-L2 | G-L3 | T-L4 |
|---|---|---|---|---|
| A-L1 | L1 ● | L1/L2 ○ | L1/L3 ○ | L1/L4 ○ |
| C-L2 | L1/L2 ○ | L2 ○ | L2/L3 ● | L2/L4 ○ |
| G-L3 | L1/L3 ○ | L2/L3 ● | L3 ○ | L3/L4 ○ |
| T-L4 | L1/L4 ○ | L2/L4 ○ | L3/L4 ○ | L4 ○ |

Figure 5a

Table 2. Unique Base Codes

| Detection Signal | L1 | L2 | L3 | L4 |
|---|---|---|---|---|
| Base combination | AA | CC | GG | TT |

Table 3. Equivalent Base Codes

| Detection Signal | L1/L2 | L1/L3 | L1/L4 | L2/L3 | L2/L4 | L3/L4 |
|---|---|---|---|---|---|---|
| Base combination 1 | AC | AG | AT | CG | CT | GT |
| Base combination 2 | CA | GA | TA | GC | TC | TG |

MULTIPLEX NUCLEIC ACID DETECTION METHODS AND SYSTEMS

CROSS REFERENCE TO RELATED APPLICATIONS

This application is a divisional of U.S. application Ser. No. 13/252,095, filed on Oct. 3, 2011, which is a continuation of International Application no. PCT/US2010/029777, filed on Apr. 2, 2010, which was based on, and claims the benefit of, and priority to, U.S. Provisional Patent Application Ser. Nos. 61/166,479 and 61/166,553 filed on Apr. 3, 2009, 61/172,660 filed on Apr. 24, 2009, and 61/266,037, filed on Dec. 2, 2009, the entire disclosures of which are hereby incorporated by reference in their entireties.

BACKGROUND

Field of Invention

The present invention relates to methods and systems for single molecule based nucleic acid amplification and subsequent detection of nucleic acid molecules, and particularly to the determination of SNPs, mutations, and to the diagnosis of diseases associated with the changes of these nucleic acid molecules.

Description of Related Art

Polymerase chain reaction (PCR) has been widely used in many areas of nucleic acid analysis for decades. Single molecule based PCR, also known as digital PCR, is a relatively new development of PCR technology. In single molecule PCR, the sample is diluted and divided into many individual nucleic acid amplification reactions, with less than one copy of template on average for each reaction. Some of the reactions have no template molecule, some have more than one copy of template molecules, and a certain percentage of the reactions have just one copy of the template. All the reactions are carried out in parallel. The nucleic acid amplicons in these reactions that start with just one copy of template molecule can be detected with methods known in the art. The analytical results provide either "yes" or "no" binary signals, as if in a digital format 0 or 1, with regard to whether a particular target molecule of interest is in the sample. Results from all the reactions in a digital PCR are statistically analyzed for quantitation of the target molecule. Digital PCR transforms the exponential amplification of conventional PCR into a linear relationship, and converts traditional analogue signals into a digital format. More detailed description of digital PCR can be found in Vogelstein et al. *Proc. Natl. Acad. Sci. USA*, 1999, 96, pp. 9236-9241, and U.S. Pat. No. 6,143,496, all herein are incorporated by reference.

The application of digital PCR includes mutation detection for early cancer diagnosis, assessing allele imbalance, prenatal genetic testing, quantification of gene expression, and DNA methylation status analysis. Pohl et al. *Expert Rev. Mol. Diagn,* 2004, 4(1):41-47; Blow, Nature Methods, 2007, 4(10):869-875; Diel et al. *Curr Opin Oncol,* 2007, 19:36-42; Dressman et al., *PNAS,* 2003, 100(15):8817-8822; Weisenberger et al. *Nucleic Acids Res.,* 2008, 36(14):4689-4698; all are herein incorporated by reference. The single molecule amplification principle that digital PCR is based on is also used in the current next-generation DNA sequencing technologies, such as Roche Life Sciences' DNA pyrosequencing technology, Life Technologies' SOLiD DNA sequencing technology, and Illumina's DNA sequencing-by-synthesis technology, for sequencing template preparation.

One of the advantages of digital PCR is its capability of detecting and quantifying rare sequence events, such as mutation, in a large background of related template molecules. This is because each amplification reaction can be independent of other target molecules in the sample due to the fact that template molecules are divided into individual PCR reactions by limiting dilution. Such capability allows for the non-invasive early cancer detection from body fluid, such as plasma and stool samples from colorectal cancer patients, as described in Diehl et al. *PNAS,* 2005, 102(45): 16368-16373; Diehl et al. *Gastroenterol.,* 2008, 135(2):489-498; all are herein incorporated by reference. This technology also enables non-invasive prenatal genetic testing in the presence of maternal DNA, as described in Lo et al., *PNAS,* 2007, 104(32):13116-13121, which is herein incorporated by reference.

The quantitation with digital PCR is carried out by counting discrete positive PCR reactions in the sample. The differentiation between mutant and wild-type DNA molecules is achieved by determining the identities of the resulting amplicons. The ratio of mutant to wild-type DNA molecules is statistically calculated from these results. Digital PCR can also be used for absolute quantitation of target molecules. More details of digital PCR quantitation can be found in: Dube et al., PLoS ONE, 2008, 3(8), e2876; Warren et al. "The Digital Array Response Curve", unpublished, Stanford University website thebigone.stanford.edu/quake/publications/DigResCurve.pdf; all are herein incorporated by reference. The precision and accuracy of digital PCR could be improved by increasing the number of target molecules being analyzed, i.e. more PCR reactions being screened in parallel for the measurement.

Currently, digital PCR is performed in a 384 well plate or a 48x770 Digital Array Nanofluidic Biochip from Fluidigm Corporation (South San Francisco, Calif., US). The majority of these applications utilize real-time PCR to analyze the amplicons in each reaction. There are reports of a method named BEAMing that generates nucleic acid amplicons on magnetic beads by emulsion PCR and uses flow cytometry to detection and counts those beads with amplicons. However, these digital PCR methods have limited multiplex capability because of the limitation of optical resolution of available fluorescent dyes.

Other means of generating nucleic acid amplicons from a single molecule include rolling circle amplification (RCA). RCA is an isothermal amplification method in which a nucleic acid probe is either hybridized or ligated onto a target nucleic acid molecule whose sequence is subsequently duplicated many times using a primer that is complimentary to part of the probe sequence. More detailed description of RCA and its applications can be found in Eriksson et al., J. Microbiol. Methods, 2009, 78, 195-202; Baner et al., Nucl. Acids Res., 1998, 26(22):5073-5078; Baner et al., Curr. Opinion Biotech., 2001, 12, 11-15; all are herein incorporated by reference. RCA is also used in sample preparation for the next generation of DNA sequencing, Drmanac et al., Science, 2010, 327:78-81, which is herein incorporated by reference.

SUMMARY

In one aspect, the present invention provides a method for determining the identity code of identity sequence tags, comprising: (a) immobilizing a plurality of analyte molecules on a surface, wherein each analyte molecule comprises an identity sequence (IS) tag that is accessible to a probe for hybridization; (b) hybridizing a pair of labeled IS probes (LISPs) from a specified pool of LISP probes with the IS tags at base interrogation positions, thereby the pair of LISPs are juxtaposed, wherein each LISP probes comprises: (i) a sequence complimentary to the IS tag sequence it hybridizes to, and (ii) a label associated with a designated base at the base interrogation positions; (c) ligating the pair of juxtaposed LISPs with a DNA ligase; (d) detecting the presence of the labels on the ligated pair of LISPs on the IS tags of the analyte molecules, and elucidating the base composition at the base interrogation positions of the IS tags according to the label combination of said ligated pair of LISPs; (e) denaturing the ligated pair of LISPs from said analyte molecule; (f) repeating steps (b) to (e) until all base positions in the IS tags are interrogated without duplication and all base composition of the IS tags are elucidated; and (g) determining the ID codes of the IS tags on said analyte molecules by comparing the base composition to designated ID codes.

In some embodiments, two specified base positions on the IS tags and one on each side of said paired probes are interrogated in each ligation cycle. In some embodiments, there are two sets of probes in each pool of LISPs, with one set being the 3' labeled IS probes (3'-LISPs) that comprise 5' phosphate groups and 3' labels, and the other set being the 5' labeled IS probes (5'-LISPs) that comprises 5' labels and 3' hydroxyl group.

In some embodiments, there are four different labels on both sets of LISPs with each label representing a designated base (A, C, G, T) at the base interrogation positions, and wherein all probes required for all possible base combinations at the interrogation positions are included in each pool of LISPs. In some embodiments, a different pool of LISPs is used in each ligation cycle; and different base positions on the IS tags are sequentially interrogated in each ligation cycle.

In some embodiments, the labels on the LISP are fluorescent dyes, electrochemical labels or nanoparticles.

In some embodiments, the base interrogation positions are within 5 bases, and preferably within 3 bases, from the ligation point of each LISP, to maintain the base recognition specificity in said paired-probe ligation.

In another aspect, the present invention provides method of analyzing target nucleic acid sequences in a sample, comprising: (a) generating from a sample a plurality of first template molecules and a plurality of second template molecules, wherein the first template molecules comprise the sequence of a first target nucleic acid and a first identity sequence (IS) tag, and the second template molecules comprise the sequence of a second target nucleic acid and a second IS tag, and wherein the first IS tag comprises a first identification (ID) code and the second IS tag comprises a second ID code; (b) generating a first cluster of nucleic acid amplicons by nucleic acid amplification of the first template molecules and a second cluster of nucleic acid amplicons by nucleic acid amplification of the second template molecules in parallel individual reactions on a surface, wherein the first cluster of nucleic acid amplicons and the second cluster of nucleic acid amplicons are spatially separated; (c) identifying the ID codes of the IS tags of the nucleic acid amplicons to determine the target nucleic acid sequences represented by the nucleic acid amplicons.

In some embodiments, the method further comprises determining the corresponding sequence variations of the target nucleic acid sequences by analyzing the sequence variations of the first clusters of the nucleic acid amplicons and said second clusters of the nucleic acid amplicons on said surface.

In some embodiments, said first and second target nucleic acid sequences can be the same or different; and there can be more than said first and second target nucleic acid sequences.

In some embodiments, the method further comprises immobilizing the first and second clusters of nucleic acid amplicons on said surface.

In some embodiments, the first and second clusters of nucleic acid amplicons are generated on the surface through enzymatic amplification or replication, wherein at least one of the primers used in the amplification or replication are attached to the surface and spatially separated during the nucleic acid amplification.

In some embodiments, the nucleic acid amplification is carried out in a plurality of individual aqueous droplets on a surface, and each droplet comprises reagents for DNA amplification, including a plurality of primers.

In some embodiments, the individual aqueous droplets are formed by a water-in-oil emulsion on said surface, and an oil phase of said water-in-oil emulsion comprising a water immiscible liquid includes a mineral oil.

In some embodiments, the DNA amplification is polymerase chain reaction (PCR), and said surface is thermal cycled during the nucleic acid amplification.

In some embodiments, the nucleic acid amplification of template molecules is carried out in hydrophilic reaction sites generated on an otherwise hydrophobic surface, wherein each hydrophilic reaction site comprises the aqueous droplets. In some embodiments, the hydrophilic reaction sites are surrounded by a hydrophobic surface of a water immiscible-liquid to prevent evaporation of aqueous phase and to isolate each individual hydrophilic reaction site during the nucleic acid amplification.

In some embodiments, the DNA amplification is polymerase chain reaction (PCR), and the surface is thermal cycled during the nucleic acid amplification.

In some embodiments, the nucleic acid amplification or replication is carried out through circularization of single stranded template molecules and subsequent isothermal rolling circle amplification by a DNA polymerase, on extension oligonucleotides attached at 5' ends on said surface of microparticles, and the extension oligonucleotides are complementary at 3' ends to the circularized template molecules and comprise free 3'-OH groups for enzymatic extension.

In some embodiments, some of the said individual aqueous droplets further comprise at least one microparticle comprising at least one of said primers attached on surface.

In some embodiments, the microparticle is a magnetic microparticle. In some embodiments, the surface of the microparticle comprises silica or polystyrene.

In some embodiments, the nucleic acid amplicons are generated on the surface of said magnetic microparticle. In some embodiments, the magnetic microparticle is immobilized on said surface by a physical force or by a chemical linkage. In some embodiments, the physical force is magnetic field.

In some embodiments, the ID codes of the nucleic acid amplicons are simultaneously determined by sequential ligation cycles of labeled probes, or by DNA polymerase sequencing technologies, wherein the ID codes reveal the representation of target nucleic acid sequences by each cluster of amplicons.

In some embodiments, the sequence status of each cluster of nucleic acid amplicons, including, but not limited to, single nucleotide polymorphism, mutation, or methylation status, is determined by nucleic acid analysis methods known in the art.

In a further aspect, the present invention provides an apparatus for analyzing target nucleic acid sequences in a sample, comprising: at least one removable flow cell comprising a first reaction surface, wherein at least one biological reaction is implemented, and a second surface comprises an optical detection window; a temperature regulating control unit comprising a heat conducting layer and associated heating and cooling elements, whereupon said first reaction surface of said removable flow cell is close in contact and temperature controlled; a magnetic unit disposed adjacent to the heat conducting layer of said temperature regulating unit, wherefrom a magnetic field can be applied to the said first reaction surface of the removable flow cell when required; a fluidic control unit connected to the removable flow cell for reagent delivery and removal; an optical detection unit for detecting optical signals from the said first reaction surface of the removable flow cell; and an electronic control unit for controlling all modules on the apparatus, and performing data analysis.

In some embodiments, the temperature regulation is affected by heating and cooling elements, including thermal electric coolers and resistive heater, or by circulation of heated and cooled fluids. In some embodiments, there is a thermal insulation layer in between the heat-conducting layer and the magnetic unit, wherein the removable flow cell is located on the heat conducting layer for temperature regulation of the first reaction surface. In some embodiments, the magnetic unit comprises an electromagnetic mechanism or a permanent magnet. In some embodiments, the system comprises a plurality of removable flow cells, enabling parallel multiple sample analysis.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 5a: Table 1 shows an example of color codes and corresponding base compositions of possible ID codes from a IS tag. FIG. 5b: Table 2 shows unique base codes. Table 3 shows equivalent base codes.

DETAILED DESCRIPTION

Figure 1A:
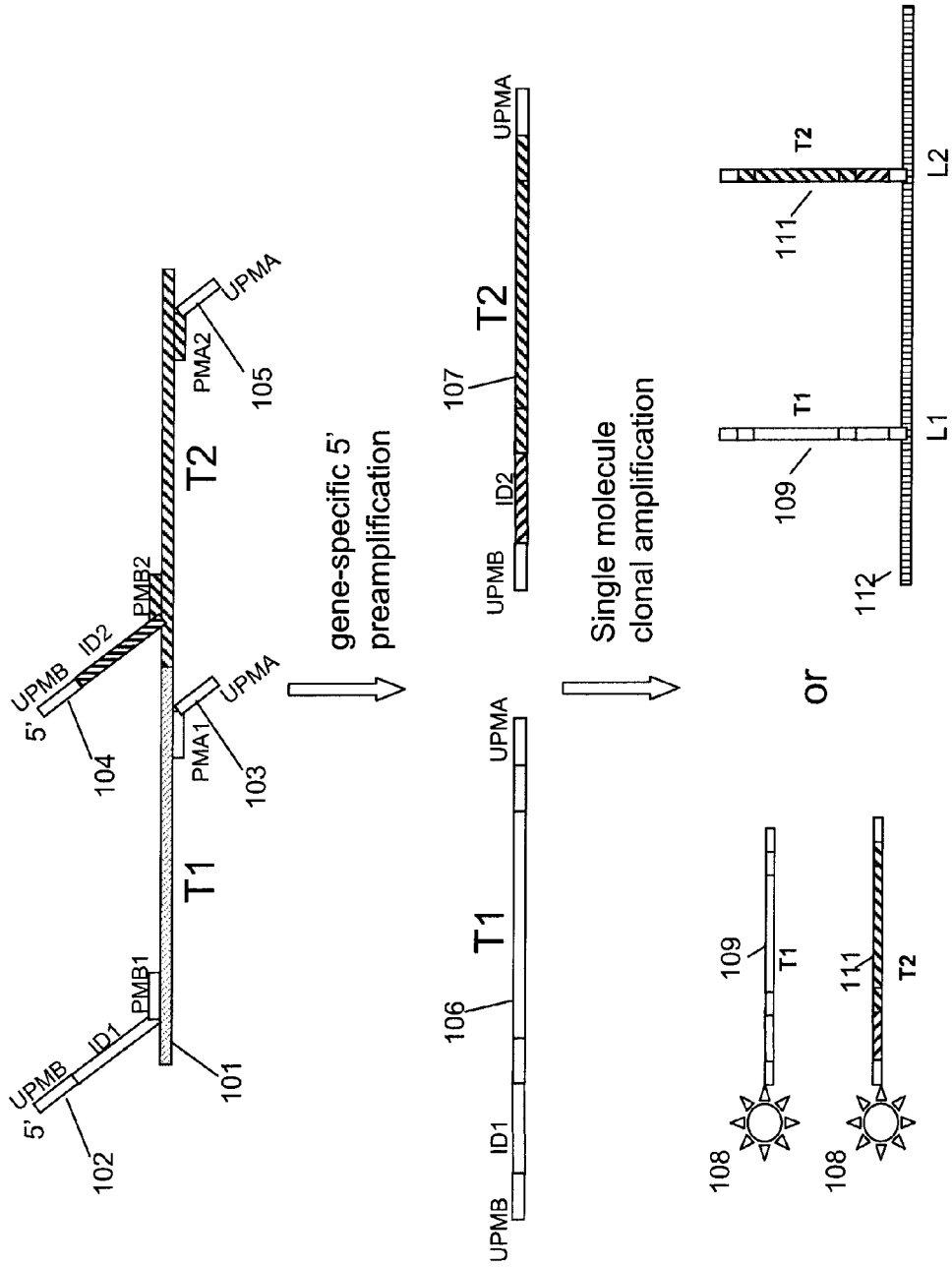
FIG. 1a is a schematic illustration of a method of incorporating IS tag into template molecules and nucleic acid amplification.

Reference will now be made in detail to the present embodiments of the invention, examples of which are illustrated in the accompanying drawings. Wherever possible, the same reference numbers are used in the drawings and the description to refer to the same or like parts.

The present invention provides methods and systems for simultaneous analysis of multiple target nucleic acid sequences, such as panel testing of biomarkers for discovery and validation, and clinical diagnostics.

A. Multiplex Analysis of Nucleic Acid by Identity Sequence Tags

In one aspect, the present invention provides a method of analyzing target nucleic acid sequences in a sample.

By "nucleic acid" or "oligonucleotide" or grammatical equivalents herein is meant at least two nucleotides covalently linked together. A nucleic acid of the present invention will generally contain phosphodiester bonds, although in some cases, for example when the primers contain labels, nucleic acid analogs can be used. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. As used herein, the term "nucleoside" includes nucleotides and nucleoside and nucleotide analogs, and modified nucleosides such as label-modified nucleosides.

By "target nucleic acid sequence" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 100 to 10,000 base pairs, with fragments of roughly 500 base pairs being preferred in some embodiments. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As outlined herein, in some embodiments the target sequence comprises a position for which sequence information is desired, generally referred to herein as the "detection position" or "detection locus". In one embodiment, the detection position is a single nucleotide, although in some embodiments, it may comprise a plurality of nucleotides, either contiguous with each other or separated by one or more nucleotides. By "plurality" as used herein is meant at least two.

As used herein, the base which base-pairs with a detection position base in a hybrid is termed a "readout position" or an "interrogation position"; thus many of the probes of the invention comprise an interrogation position. In some embodiments, as is outlined herein, the target sequence may not be the sample target sequence but instead is a product of an amplification reaction herein, sometimes referred to herein as a "derivative" target sequence, a "template molecule", or an amplicon. By "amplicon" herein is meant a nucleic acid molecule that is produced via an amplification method. Typically, the amplification is by a PCR method, including multiplex PCR. The amplicon may be a double stranded or a single stranded DNA molecule. As discussed below, techniques that enrich for one strand of an amplification reaction can be used.

In one embodiment, the amplicons of the present invention include target nucleic acid sequences. In another embodiment, the amplicon contains a nucleic acid target strand amplified by a method described herein that contains two or more target domains as described below and second nucleic acid target strand that is complementary to the first nucleic acid strand. By a "single stranded target nucleic acid", "single stranded target", "single stranded target sequence" or grammatical equivalents thereof, is meant the starting material for the amplification methods of the present invention. In another embodiment, a target sequence of the present invention contains a region that is substantially complementary to a probe sequence, as defined herein.

The sample comprising the target sequence may be virtually from any organism, and any sources, including, but not limited to, bodily fluids (including, but not limited to, blood, bone marrow, urine, feces, tears, serum, lymph, saliva, anal and vaginal secretions, perspiration, semen, and other bodily fluids of virtually any organism, such as mammalian, including human, samples); cell lysates of bacteria and pathogens, including virues; hard tissues (e.g. organs such as liver, spleen, kidney, heart, lung, etc.); environmental samples (including, but not limited to, air, agricultural, water and soil samples); biological warfare agent samples; research samples (i.e. the sample may be the products of an amplification reaction, including both target and signal amplification as is generally described in WO99/037819 incorporated herein by reference, such as a PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

If required, the target sequence is prepared using known techniques. For example, the sample may be treated to lyse the cells, using known lysis buffers, electroporation, etc., with purification and/or amplification occurring as required, as will be appreciated by those in the art.

In one aspect, the present invention provides a method of gene-specific pre-amplification that incorporates specific IS tag and IS code into the amplicons generated based on the target nucleic acid sequences.

Gene-specific pre-amplification has been widely used for sample preparation in nucleic acid analysis such as genotyping, gene expression analysis, and clinical diagnosis. Li et al., Nucleic Acids Res., 1996, 24:538-539; Mengual et al., BMC Research Notes, 2008, June, 1:21; Xia et al., Genet. Mol. Biol.; 2009:20-24; Arneson et al., Cold Spring Harb. Protoc., "Whole-Genome Amplification by Improved Primer Extension Preamplification PCR (I-PEP-PCR)", 2008; all are herein incorporated by reference.

In some embodiments, the method of the invention comprises generating from a sample a plurality of first template molecules and a plurality of second template molecules, the first template molecules comprise the sequence of a first target nucleic acid and a first identity sequence (IS) tag, and the second template molecules comprise the sequence of a second target nucleic acid and a second IS tag, and the first IS tag comprises a first ID code and the second IS tag comprises a second ID code.

In some embodiments, the first and second template molecules are generated through an enzymatic reaction, using primers comprising the IS tags and sequences that are complimentary to at least part of the target nucleic acid sequences, wherein the quantity ratios of the two target nucleic acid sequences in the sample are preserved.

By "identity sequence (IS) tag" herein is meant a short artificial DNA sequence that is used to encode a target molecule, as a way for identifying a specific target among analytes in a sample. In some embodiments, the IS is less than, 6 bases, or less than 10 bases in length. IS tags may also comprise additional nucleic acid sequences that are needed for probe hybridization during decoding process. IS tags are generally designed to be unique from the sequence of the genome of interest in nucleic acid analysis. In some embodiments, these IS tags are introduced as part of sample preparation.

By "identity (ID) code" herein is meant a code assigned to an IS tag. The base composition of each IS tag corresponds to a specific ID code.

In some embodiments, the first and the second target nucleic acid sequences are similar in abundance. In some embodiments, the first target nucleic acid sequences is at least 100, 1000, or 10,000 times more abundant than the second target nucleic acid sequence.

In some embodiments, the method of the present invention comprises generating a first cluster of nucleic acid amplicons by nucleic acid amplification of the first template molecules and a second cluster of nucleic acid amplicons by nucleic acid amplification of the second template molecules, wherein the first cluster of nucleic acid amplicons and the second cluster of nucleic acid amplicons are located spatially separately.

By "nucleic acid amplicons" or "amplicon clones" herein is meant a population of amplicons that can be traced directly or indirectly to an isolated polynucleotide. By "nucleic acid amplification" herein is meant of method of isolating and amplifying polynucleotides to yield "amplicon clones" or "nucleic acid amplicons".

By "located spatially separately" herein is meant that two or more clusters of amplicons are located separately in space. For example, the different clusters of amplicons can locate on different spots on the same surface, or locate on different surface, such as on the surface of different microparticles as described herein.

In some embodiments, the first and second clusters of nucleic acid amplicons are generated on the surface through enzymatic amplification or replication, wherein at least one of the primers used in the amplification or replication are attached to the surface and spatially separated during the nucleic acid amplification.

In some embodiments, the clusters of nucleic acid amplicons are attached on a surface. The nucleic acid amplicons are attached to the surface directly or indirectly. In some embodiments, the nucleic acid amplicons are attached to the surface of a magnetic microparticle, and the magnetic microparticle is immobilized on the surface by a physical force (e.g. magnetic field) or by a chemical linkage described herein or known in the art.

In some embodiments, the ID codes of the IS tags of said nucleic acid amplicons are identified to determine the target nucleic acid sequences represented by the nucleic acid amplicons as described herein.

In some embodiments, the corresponding sequence variations of the target nucleic acid sequences are determined by analyzing the sequence variations of said clusters of nucleic acid amplicons.

By "sequence variations" herein is meant the characteristics of a sequence, such as single nucleotide polymorphism, mutation, or methylation. Sequence variations can be determined by the methods known in the art or disclosed herein, including, but not limited to labeled probe ligation, single-base extension, DNA sequencing, and melting curve analysis.

In some embodiments, the method of the present invention further comprises quantifying the number of the clusters of nucleic acid amplicons from each template molecule, by adding all identified clusters of nucleic acid amplicons that contain a specific IS tag assigned to the template molecule to infer the amount of each target nucleic acid sequence in the sample, knowing the dilution factors used in the analysis.

In general, the random distribution of template molecules in single molecules nucleic acid amplification follows Poisson distribution. The random distribution of M template molecules in C reaction chamber follows Poisson distribution. The probability of having at least one template molecule in a given reaction chamber is denoted as p, $$p = 1 - \left(1 - \frac{1}{C}\right)^M$$

and the average concentration of template molecule in each reaction chamber is denoted by λ:

$$\lambda = M/C$$

As the number of reaction chambers becomes arbitrarily large, one can get, $$\lambda = -\ln(-p)$$

The probability p can be estimated by counting the positive reaction chambers in digital PCR. Thus, the average concentration of the template molecule in each reaction chamber and consequently the amount of target molecules in the sample can be statistically calculated.

For 95% confidence interval, the confidence limits of probability p can be expressed as $$p \pm 1.96 \sqrt{\frac{p(1-p)}{C}}$$

In some embodiments, the method of the present invention comprises using certain target sequences that have known amount of copies in each genome of interest, such as house keeping genes, as quantification reference sequences in the analysis.

B. Preparation of Template Molecules with Embedded Identity Sequence Tags

Although the present invention has been described in considerable detail with reference to certain embodiments thereof, other embodiments are possible. Therefore, the spirit and scope of the appended claims should not be limited to the description of the embodiments contained herein.

Figure 1B:
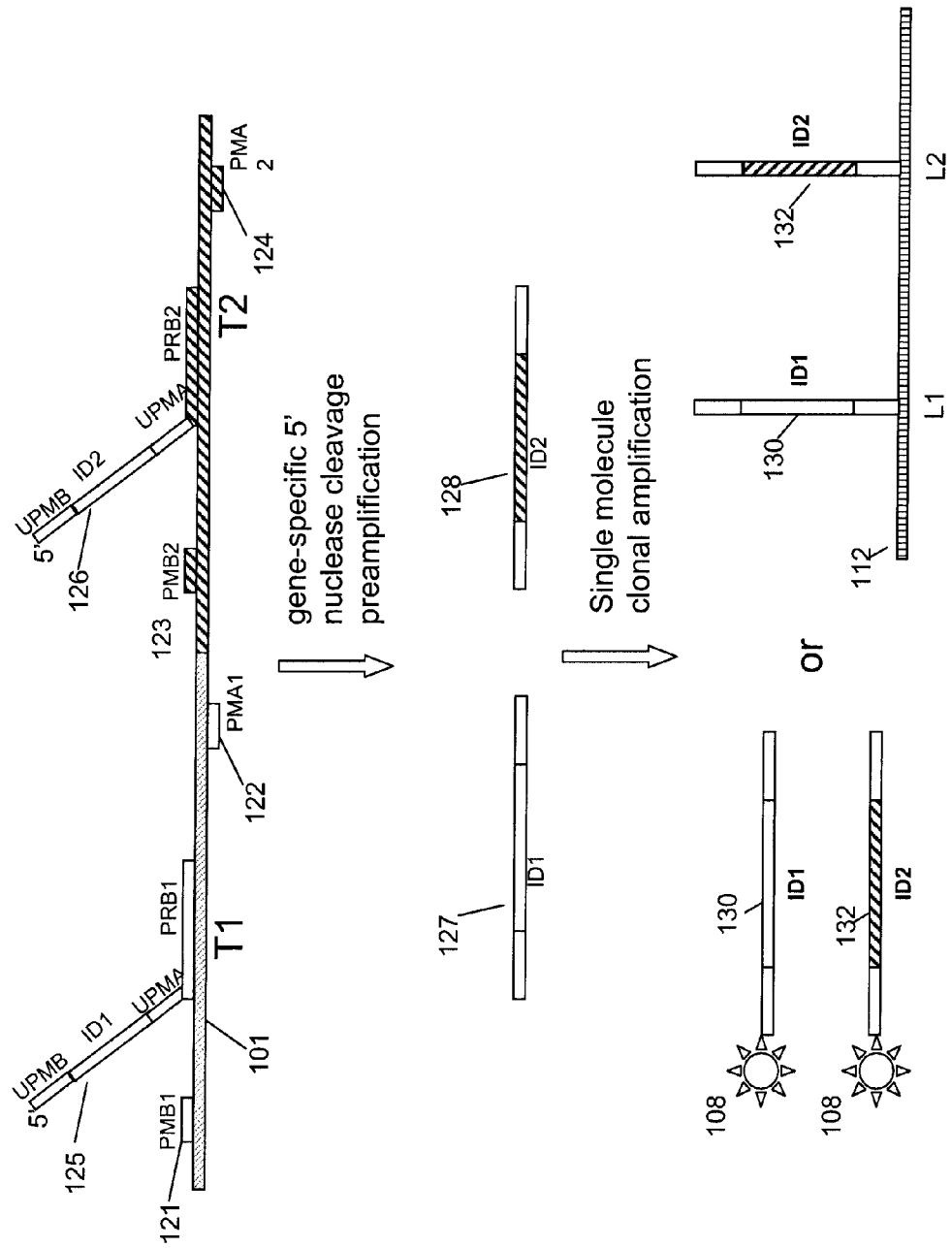
FIG. 1b is a schematic illustration of another method of incorporating IS tag into template molecules and nucleic acid amplification.
Figure 1C:
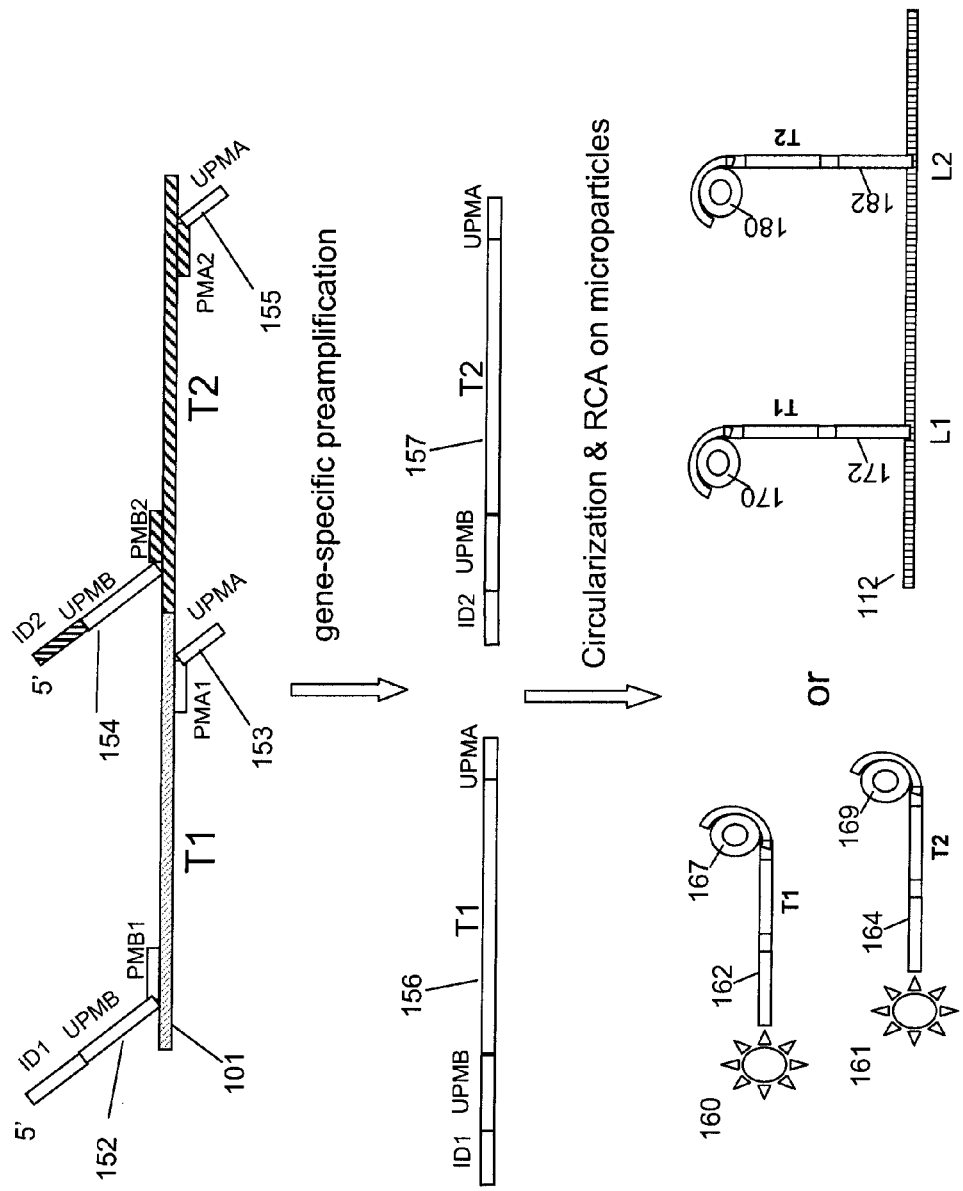
FIG. 1c is a schematic illustration of a method of incorporating IS tag into template molecules and nucleic acid amplification by single molecule rolling circle amplification.

Some exemplary embodiments are shown in FIGS. 1a to 1c which illustrate the methods of generating template molecules with IS tag incorporation and subsequent nucleic acid amplification of the template molecules on surface. The template molecules can be prepared from target sequences by gene-specific pre-amplification using IS tag embedded primers as in illustrated in FIG. 1a, or by gene-specific 5' nuclease cleavage preamplification as illustrated in FIG. 1b. 101 is the target molecule of interest, such as genome DNA, with at least one target sequence. One of the primers in the gene-specific preamplification, shown as 102 in FIGS. 1a and 152 in FIG. 1c for target sequence T1, contains a unique IS tag sequence having identity code ID1 and the sequence of a universal primer (UPMB), as well as sequence (PMB1) that is complimentary to part of the target sequence T1. The other primer in the preamplification primer set for target sequence T1, 103 in FIG. 1a and 153 in FIG. 1c, also contains the sequence of a universal primer sequence (UPMA) and sequence (PMA1) that is complimentary to part of target sequence T1. Similarly, another primer, 104 in FIGS. 1a and 154 in FIG. 1c, contains another unique IS tag sequence having identity code ID2, universal primer sequence UPMB, and sequence complimentray to part of target sequence T2; and primer 105 in FIGS. 1a and 155 in FIG. 1c contains universal primer sequence UPMA and sequence complimentary to part of target sequence of T2. The template molecules obtained from the gene-specific preamplification are 106 in FIGS. 1a and 156 in FIG. 1c identified by IS tag ID1; and 107 in FIG. 1a and 157 in FIG. 1c identified by IS tag ID2.

In some embodiments, asymmetric PCR preamplification is used to generate single stranded template molecules for ligation and nucleic acid amplification by RCA on the extension oligonucleotides.

The gene-specific preamplification in the template molecule preparation describe in this invention can be accomplished in relatively small number of PCR cycles, preferably less than 30 cycles, 25 cycles, or 20 cycles, to provide sufficient template molecules and to preserve the ratios among different target sequences in the original sample.

In some embodiments, the method of generating IS tag embedded template molecules from target sequences is illustrated in FIG. 1b. Gene-specific probes 125 and 126 for target sequences T1 and T2 respectively have 5' flaps that contain gene specific IS tags ID1 and ID2 as well as universal primer sequences UPMA and UMPB. Similar to TaqMan real-time PCR probes, these 5' flaps are cleaved from the probes during gene-specific 5' exonuclease cleavage preamplification with gene-specific primer sets 121 and 122 for target T1, 123 and 124 for target T2. Polymerases with 5' to 3' exonuclease activity, such as Taq polymerase, degrade the part of the probes 125 and 126 that are annealed to the target sequences during PCR, releasing the 5' flaps in solution. Such cleaved 5' flaps 127 and 128 with embedded IS tags ID1 and ID2, shown in FIG. 1b, become surrogates of the original target sequences T1 and T2, and serve as template molecules in subsequent analysis.

Because the probes used in the 5' exonuclease cleavage preamplification are specifically designed for target sequences of interest, the presence or absence of the IS tag sequences, ID1 and ID2 in this example, in the final results can reveal the sequence information of these target sequences in the original sample. For example, if the genomic DNA 101 in FIG. 1b is sodium bisulfite-treated for DNA methylation analysis, methylation specific primers and probes can be used in the 5' exonuclease cleavage preamplification of the target sequences. The presence or absence of the IS tags in the final analysis, depending on the design of the assay, will indicate whether the target sequences in the original sample are methylated.

C. Single Molecule Nucleic Acid Amplification on Surface

The template molecules obtained by the methods described herein are subsequently amplified based on single molecule based nucleic acid amplification, wherein the amplification starts from a single copy of template, in order to generate clusters of nucleic acid amplicons for further analysis. The amount of amplicons on each positive microparticle or reaction spot on the surface can be more than tens of thousands or hundreds of thousands after the amplification. Hundreds of thousands or millions of positive microparticles or reaction spots on surface can be generated in an assay as disclosed herein, depending on the desired size of analysis. There are various methods of implementing the single molecule nucleic acid amplification described herein.

In some embodiments, the nucleic acid amplification is by polymerase chain reaction (PCR) that produces amplicons on microparticles or a continuous surface, as shown in FIGS. 1a and 1b. The template molecules are distributed into a large number of parallel individual PCR amplification reactions wherein there is less than one copy of the template molecules on average in each individual PCR reaction. Dilution of template molecules might be needed to achieve the goal of less than one copy of template molecule in each individual PCR. One of the universal primer sequences, complimentary to UPMA and UPMB in FIGS. 1a and 1b, can be attached to the surface of a solid support, such as magnetic microparticles 108 or a flat surface 112, so that clusters of the resulting nucleic acid amplicons are spatially separated on the surface. The resulting amplicons 109 and 111 for genes T1 and T2 respectively contain the target sequences and corresponding IS tags. The use of universal primer sequences simplifies the assay design. In another embodiment of this invention, instead of using universal primer sequences, gene-specific primer sequences can be used in the nucleic acid amplification. Cluster of nucleic acid amplicons lessens the requirements for detection.

In some embodiments, the nucleic acid amplification is carried out in a plurality of aqueous droplets, each droplet comprising: reagents for DNA amplification, including a plurality of primers, and a microparticle with at least one of the primers attached on its surface.

In some embodiments, the microparticle are magnetic particles. The size of these magnetic particles can range from less than 1 micron to 100 microns, preferably less than 30, preferably less than 20, and more preferably between 1 to 10 microns. The surface of the microparticle comprises materials such as silica or polystyrene, or the like.

In some embodiments, the aqueous droplets are formed by water-in-oil emulsion and are contained in a reaction vessel, wherein said reaction vessel contains an oil phase comprising a water immiscible liquid.

In some embodiments, the nucleic acid amplification of template molecules is carried out on hydrophilic reaction spots patterned on an otherwise hydrophobic surface, wherein each hydrophilic reaction site comprises the aqueous droplets. In some embodiments, the hydrophilic reaction sites are surrounded by a hydrophobic surface of a water immiscible liquid (e.g. mineral oil) to prevent evaporation of aqueous phase and to isolate each individual hydrophilic reaction sites during the nucleic acid amplification.

In some embodiments, the DNA amplification is polymerase chain reaction (PCR), and the reaction vessel, or the otherwise hydrophobic surface, is thermal cycled during the nucleic acid amplification.

In some embodiments, the surface of a solid support is used for this disclosed invention, and clusters of primers are directly attached to the surface at predetermined locations, known as reaction spots, and individual amplification reactions on these reaction spots are physically isolated from each other on the surface. The size of these reaction spots can range from 10 to 200 microns, preferably less than 100 microns, and more preferably less than 50 microns. The materials of the solid support can include glass, silicon, polymeric material and other materials known in the art that are compatible with PCR reactions and fluorescence detection.

The attachment of primers to magnetic microparticles or the solid support can be accomplished through various surface chemistry know in the art, c.f. Hermanson, "Bioconjugate Techniques", Academic Press, 1996, herein is incorporated by reference. The universal primer on the magnetic microparticles or on the surface serves as one of the primers for the nucleic acid amplification. It is preferred that the complimentary UPMA sequence is attached to the surface of the support, which results in amplicons having the IS tags away from the surface for efficient hybridization by probes in ensuing detection steps. However, the complimentary UMPB can also be attached to the surface for single molecule amplification if the assay design necessitates such an approach. A small amount of the primer that is attached to the magnetic microparticles or surface can be included in the aqueous PCR reaction mix to facilitate the initial cycles of the amplification. Such use of the primers has been reported in the literature.

In some embodiments, the single molecule nucleic acid amplification is conducted with rolling circle amplification (RCA) on surface. As illustrated in FIG. 1c, the template molecules is circularized and extended on extension oligonucleotides that are attached on microparticles or on a surface. The extension oligonucleotides serve as both the template for the circularization and primers for the rolling circle extension of the template molecules. It is critical to have just one copy of the circularized template molecule on each microparticle or at each reaction site on the surface in single molecule rolling circle amplification, to ensure that the quantification of the extension products reflects the amount of the template molecules in the original sample.

In some embodiments, the single molecule nucleic acid amplification is carried out by water-in-oil emulsion PCR (emPCR). Magnetic microparticles with one of the universal primers attached, together with other reagents needed for PCR, can be included in the aqueous phase in emPCR, nucleic acid amplicons are generated on the surface of magnetic microparticles when there is only one template molecule present in the reaction droplet. Droplets in the emulsion can range from 5 to 200 microns, and more preferably between 10 to 50 microns, depending on the size of microparticles used. Detergent is normally included in the oil phase to keep the emulsions stable during PCR thermal cycling. Methods and devices needed for making emulsions are known in the art. U.S. Pat. No. 7,323,305 and U.S. Patent Appl. Pub. No. 2009/0035825; all are herein incorporated by reference. The thermal cycling can carried in wells of a 96 well or 384 well plate on a commercial thermal cycler. The art of thermal cycling for PCR is well known in the art.

Figure 2:
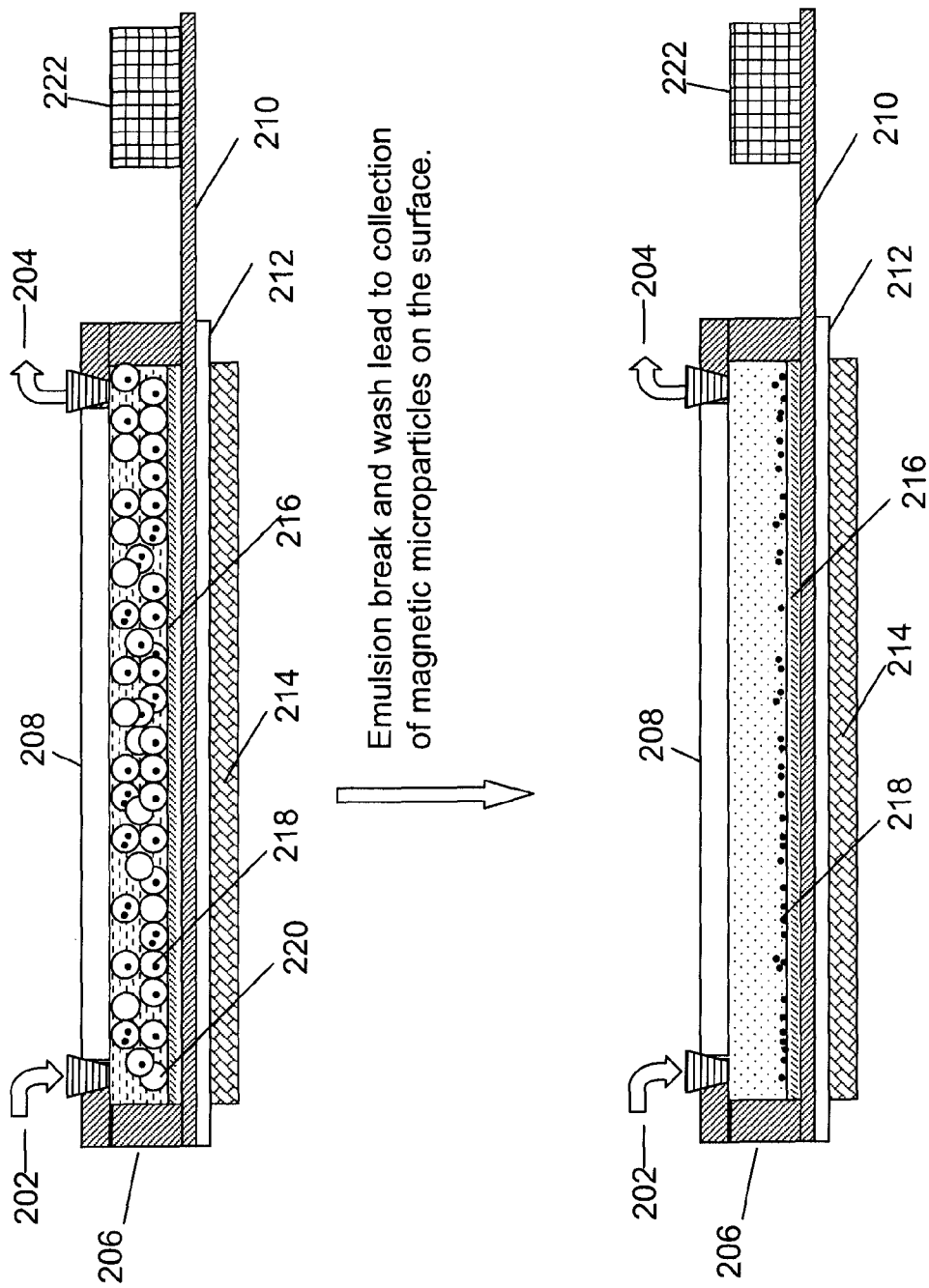
FIG. 2 is a schematic illustration of a removable flow cell and the distribution of magnetic microparticles inside it.

In some embodiments of this invention, the emulsion is directly transferred into a flow-cell assembly after thermal cycling, such as the one illustrated in FIG. 2. The flow-cell comprises a detection widow 208, flow-cell housing 206, fluidic inlet 202, fluidic outlet 204, substrate 216, emulsion droplets 220 and magnetic microparticles 218. The flow-cell is place on a thermal conducting plate 210 that is attached to an electric thermal heating and cooling device 222. A permanent magnet 214 is placed underneath separated by a thermal isolation layer 212 from the thermal conducting plate 210. The temperature of the substrate 216 is regulated through the thermal conducting plate. The substrate 216 can be made of various materials that can transfer heat through the substrate, has low background fluorescence, and is compatible with enzymatic reactions on the surface. Examples of the substrate can be glass, quartz, and silicon. The thermal conducting plate is made of good thermal conductors, such as copper and aluminum. The transfer of emulsion into the flow-cell can be performed through various methods known in the art, such as manual pipette and syringe pump.

The emulsion floats in the flow-cell keeping individual droplets when first filling the flow-cell. The magnet 214 can be optional removed from the substrate 216 in this step. An emulsion break agent can be pumped into the flow-cell through the fluidic inlet and outlet, which demulsifies the emulsion droplets and results in the precipitation of magnetic microparticles onto the substrate surface, as illustrated in FIG. 2. The magnet underneath the flow-cell helps collect and retain these microparticles on the substrate surface. Emulsion break reagents is well known in the art and widely used, such as butanol and excessive detergents.

The magnetic microparticles in the flow-cell randomly distribute on the substrate surface after emulsion break. Depending on the microparticle density in the flow-cell, some of them will aggregate. However, the majority of them will be separated on the surface and be held in position by a magnetic field. Aggregation of microparticles is undesirable and could pose difficulties for imaging process. Due to the enormous number of aqueous droplets in emPCR, millions of magnetic microparticles can be deposited on the substrate surface in the flow-cell. After thorough washing, the amplicons on the magnetic microparticles that are retained on the surface can be used for further sequence analysis.

In some embodiments, the single molecule nucleic acid amplification is directly performed on a patterned surface that comprises hydrophilic spots surrounded by hydrophobic area, i.e. the hydrophilic spots are spatially separated from each other by the hydrophobic area. The hydrophilic spots can be made PCR compatible through surface modification. Exemplary applications of such specially patterned surface can be found in WO 2005/029041 A2 and US 2008/0153135 A1, all are herein incorporated by reference.

Figure 3:
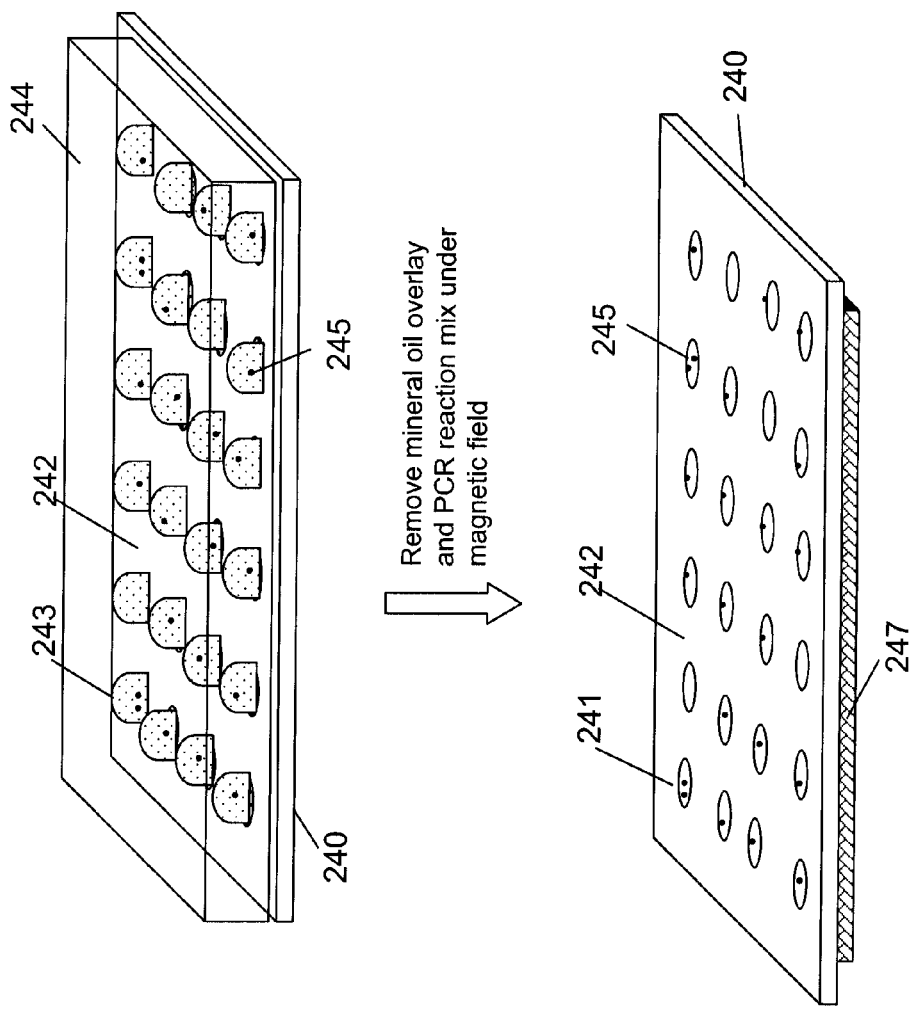
FIG. 3 shows an array of individual PCR reaction droplets containing magnetic microparticles on the patterned surface covered by an oil layer, and the retention of these magnetic microparticles by external magnetic force on the surface after the oil overly is removed.

An example of the hydrophilic patterned spots surrounded by hydrophobic surface is illustrated in FIG. 3, where 240 is the substrate on which an array of hydrophilic spots 241 is surrounded by hydrophobic area 242. In some embodiments, the hydrophilic spots comprise physical or chemical modification of the hydrophobic surface of the substrate. In other embodiments, the hydrophobic area comprises the physical or chemical modification of the hydrophilic surface of the substrate. Such modification of the surface can be either chemical derivatization or physical coating of the surface of the substrate. Several methods can be used for making such patterned surface, such as chemical derivatization of the surface by photolithography, U.S. Pat. Nos. 5,985,551 and 5,474,796; and modification through surface physical absorption, US 2008/0268440, all are herein incorporated by reference.

Aqueous solutions can be self driven to the hydrophilic spots surrounded by hydrophobic surface area, forming an array of individual aqueous droplets on the surface depicted as 243 in FIG. 3. This is due to the surface interaction between the aqueous solution and such patterned surface. The surface tension difference between the hydrophilic spots and highly hydrophobic area dictates the distribution of the aqueous solution on the surface. By simply flooding such patterned surface with excess aqueous solution and subsequently withdrawing the excess liquid from it, aqueous droplets will stay only on the hydrophilic spots, which effectively divides the aqueous sample into a large number of individual partitions. This method of sample partition is much faster and economical than traditional liquid dispensing methods using robotic systems.

In some embodiments, a sealing liquid can be quickly applied over the distributed individual aqueous droplets on the patterned surface to prevent evaporation during thermal cycling of PCR. The sealing liquid generally is immiscible with water, compatible with enzymatic reactions, and easily removed from the surface after thermal cycling. A preferred sealing liquid in this invention comprises mineral oil (overlay oil), as 244 depicted in FIG. 3.

The size of the patterned hydrophilic spots can very from 1 micron to 1000 microns in radius, preferably from 5 to 200 microns in radius, and more preferably from 10 to 100 microns. Examples of the droplet volume and total number of droplets that can be formed on a patterned surface with a footprint of a regular microscope slide of 2 by 3 inches (50 by 76 mm) are calculated as follows, assuming the droplets are hemisphere and with a pitch of 1.5 radius of the hydrophilic spots on the surface. This table shows the excellent capability and flexibility of this invention in terms of the number of individual reactions that can be processed in parallel in a single assay.

| Hydrophilic spot radius (μm) | Droplet volume | Total No. of droplets |
|---|---|---|
| 5 | 0.26 pL | $24 \times 10^6$ |
| 10 | 2 pL | $6 \times 10^6$ |
| 25 | 32 pL | $9.7 \times 10^5$ |
| 50 | 262 pL | $1.7 \times 10^5$ |
| 100 | 2 nL | $6 \times 10^4$ |
| 200 | 16 nL | $1.5 \times 10^4$ |

In some embodiments, magnetic microparticles 245 in FIG. 3 on which one of the universal primers is attached can be included in the PCR reaction mix and be partitioned, together with IS tag embedded template molecules and other PCR reagents, into the aqueous droplets on the patterned surface. These magnetic microparticles randomly distribute among all hydrophilic spots on the patterned surface. Some of the aqueous reaction droplets will have no magnetic microparticles, some of them will contain just one magnetic microparticle, and some of them will have more than one magnetic microparticle, depending on the amount of magnetic microparticles included in the initial PCR reaction mix. However, the existence of more than one magnetic microparticle in a particular hydrophilic reaction spot does not necessarily render them unusable. Generally, what is critical in the nucleic acid amplification is that all the amplicons in a given individual reaction are replicates of a single template molecule.

In some embodiments, a magnetic field is applied underneath the patterned surface as illustrated in FIG. 3 to confine the magnetic microparticles 245 on the patterned hydrophilic spot 241 in subsequent analysis. The magnetic filed can be applied through various techniques known in the art, such as by a permanent magnet 247.

In some embodiments, the nucleic acid amplification is by rolling circle amplification (RCA) resulting in spatially separated replicates of the template molecules, such as 156 and 157 as shown in FIG. 1 *c*. In clonal RCA amplification, the single stranded template molecules are hybridized and ligated on extension oligonucleotides 162 and 164 that contain contiguous sequences that are complimentary to both the 5' and 3' ends of the template molecules where the circularization of the template molecules can occur. These extension oligonucleotides are attached to microparticles or a surface at 5' ends, and have free —OH groups at their 3' ends that are complimentary to the circularized template molecules 167 and 169, and wherein the extension of the sequence by a polymerase can occur. The circularized template molecules serve as templates for the clonal RCA by various polymerases, such as φ29 DNA polymerase or Klenow fragment. RCA can efficiently generate up to 1,000 nt/min of the target sequence. Thousands of copies of the circularized template molecules can be generated as continuous linear sequences of the clonal RCA products. Again, the spatial separation of these nucleic acid amplicons either on a surface or on different microparticles is required for this invention.

The circularized template molecules are between 40 to 400 bases in length, and preferable between 60 to 200 bases in length.

In some embodiments, the template molecules are ligated onto the extension oligonucleotides and extended by RCA on microparticles in solution where the ratio of the template molecules to microparticles is adjusted to ensure single molecule RCA on the microparticles. The extended microparticles 160 and 161 in FIG. 1 *c* are then introduced into the flow-cell depicted in FIG. 2 for further analysis. In some embodiments, the circularized and the isothermal extension of the template molecules are carried out on the microparticles distributed on the surface beforehand in the flow-cell.

In some embodiments, the unique nucleic acid sequences at the two ends of each template molecule are the same, or different, for at least two of the different template molecules.

In some embodiments, the primers 152 and 154 in gene-specific preamplification depicted in FIG. 1*c* are designed to have IS tag sequences at the ends to make each template molecule be ligated and extended on a specific microparticle. The number of types of microparticles needs to be at least the same as that of target sequences in the assay. Such design ensures that the RCA products are copies of the same sequence on each microparticle.

In some embodiments, the primers 152 and 154 in gene-specific preamplification depicted in FIG. 1*c* are designed to have universal primer sequences at the ends of the template molecules. Such primer design requires only one type of microparticles, irrespective of the number of target sequences, in the assay.

D. Sequential Paired-Probe Ligation

The IS tag base composition is analyzed in the present invention.

Several methods known in the art, such as probe hybridization and DNA sequencing, can be used to determine the IS tag base composition. Current next-generation DNA sequencing technologies, including pyrosequencing, SOLiD sequencing, and sequencing-by-synthesis methods, can potentially be used for the base sequence determination. However, these methods are time consuming and costly. The present invention provides a novel sequential paired-probe ligation chemistry to determine the base composition at two positions in one ligation cycle.

In one aspect, the present invention provides a method for determining the identity code of identity sequence tags, comprising the steps of: (a) immobilizing a plurality of analyte molecules on a surface, wherein each analyte molecule comprises an identity sequence (IS) tag that is accessible to a probe for hybridization; (b) hybridizing a pair of labeled IS probes (LISPs) from a specified pool of LISP probes with the IS tags at base interrogation positions, thereby the pair of LISPs are juxtaposed, wherein each of the LISP probe comprises: (i) a sequence complimentary to the IS tag sequence it hybridizes to, and (ii) a label associated with a designated base at the interrogation position; (c) ligating the pair of juxtaposed LISPs with a DNA ligase; (d) detecting the presence of the labels on the ligated pair of LISPs on the IS tags of the analyte molecules, and elucidating the base composition at said base interrogation positions of said IS tags according to the label combination of said ligated pair of LISPs; (e) denaturing said ligated pair of LISPs from said analyte molecule; (f) repeating steps (b) to (e) until all base positions in said IS tags are interrogated without duplication and all base composition of said IS tags are elucidated; and (g) determining the ID codes of said IS tags on said analyte molecules by comparing said base composition to designated ID codes.

In some embodiments, two specified base positions on said IS tags, one on each side of said paired probes, are interrogated. Different base positions on said IS tags are sequentially interrogated in each ligation cycle without duplication.

Figure 4:
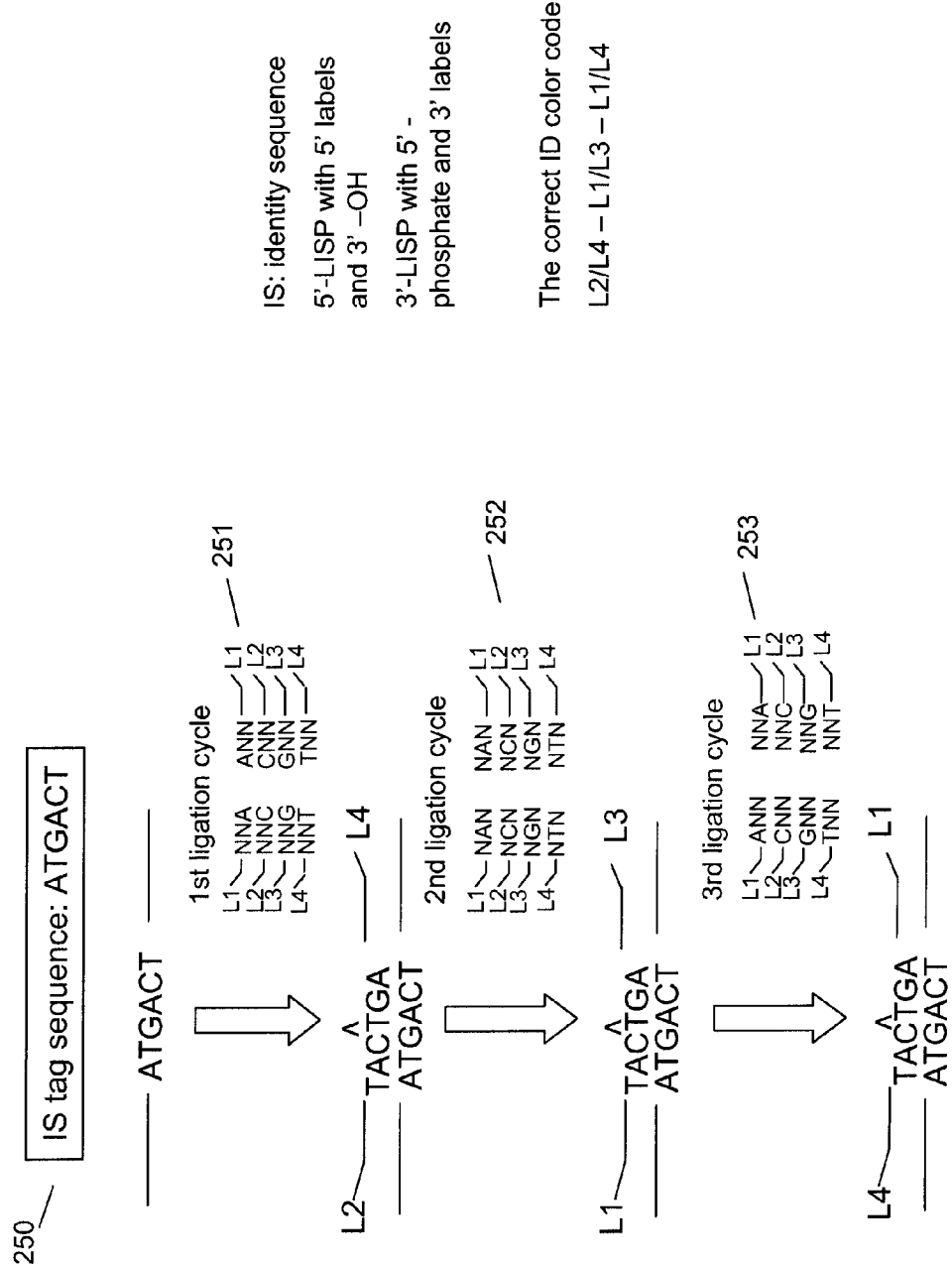
FIG. 4 depicts the principle of sequential paired-probe ligation chemistry for IS tag determination.

In some embodiments, there are two sets of probes in each pool of LISPs, with one set being the 3' labeled IS probes (3'-LISPs) that comprise 5' phosphate groups and 3' labels, and the other set being the 5' labeled IS probes (5'-LISPs) that comprises 5' labels and 3' hydroxyl group. A pool of LISPs accounts for all possible base compositions at the interrogation positions. Degenerate bases (Ns) can be used in making these LISPs in order to save time and cost, as illustrated in FIG. 4. The using of degenerate bases in oligonucleotide synthesis is known in the art.

In some embodiments, there are four different labels on both sets of LISPs with each label representing a designated base (A, C, G, T) at the interrogation position. In some embodiments, the labels on the LISP are fluorescent dyes, electrochemical labels or nanoparticles.

In some embodiments, a specified pool of LISPs is used in each ligation cycle. As used herein, a "specified pool of LISPs" is a pool of LISPs that are designed to interrogate a specific base position from the ligation point. As an example, illustrate in FIG. 4, the specified pool of LISPs used in the first ligation cycle comprises LISPs that are designed to interrogate the first bases at the ligation point. The specified pool of LISPs used in the second ligation cycle comprises LISPs that are designed to interrogate the second bases from the ligation point.

In some embodiments, the sequential paired-probe ligation chemistry for determining the base composition of the IS tags embedded in the nucleic acid amplicons on a surface is illustrated in FIG. 4. The ID codes of the exemplary 6-base IS tag 250 depicted in FIG. 4 is determined by conducting 3 cycles of paired-probe ligations. There are two sets of labeled IS probes (LISP) in each cycle of the sequential paired-probe ligation chemistry. One set of probes, 5' labeled IS probes (5'-LISPs) comprise 5' labels and 3' hydroxyl group, while the other set of probes, 3' labeled IS probes (3'-LISPs) comprise 5' phosphate group and 3' labels, as indicated by 251, 252, and 253 for $1^{st}$, $2^{nd}$, and $3^{rd}$ cycle respectively in FIG. 4. A LISP comprises a base sequence complimentary to the unique IS tag and parts of the up-stream or down-stream known sequences flanking the IS tag.

Both 3' end of 5'-LISP and 5' end of 3'-LISP contain a 3-base sequence that are designed to co-hybridize to the IS tags in juxtaposed positions and be ligated together by a DNA ligase, such as T4 ligase or Tth ligase.

In some embodiments, the ligated labeled paired-probes can remain on the template molecules, and both labels be detected on the surface by a detector. The unligated probes are removed from the surface by stringent washing. After one cycle of the paired-probe ligation, the ligated paired-probes are removed from the target molecules for next ligation cycle to proceed. The $T_m$ of the ligated paired-probes are significantly different from that of unligated probes. The removal of the ligated LISPs can be performed by denaturing, such as heating or basic solutions. Sequential cycles of the ligation are carried out until all base positions are interrogated.

The basics of "zipcode" sequence design has been studied in the art, c.f. Gerry et al. J. Mol. Biol., 1999, 292, 251-262, which is herein incorporated by reference. Not all possible base sequence combinations are suitable as IS tags, due to self-pairing or interacting with target molecule sequences. For example, palindromic sequence -ACGT- may not be a good choice as IS tag. Thus, the number of available IS tags might be less than the theoretical numbers. The length of LISP can vary from 6 to 40 bases, more preferably between 8 to 20 bases. They can preferably have similar Tm for better hybridization specificity during paired-probe ligation.

The specificity and footprint of DNA ligase has been studied by several groups, c.f. Luo et al. Nucleic Acids Res., 1996, 24(14):3071-3078; Odell et al. *J. Biol. Chem.,* 1999, 274(20):14032-14039; all are herein incorporated by reference. More than three bases on either side of the ligation site are generally selected by DNA ligase according the template base sequence. There might be more errors by ligase at base positions away from the ligation site depending on the ligase and ligation conditions. As long as there a consensus in determining an IS tag sequence on a microparticle that can have up to hundreds of thousands of amplicons, some noise can be tolerated.

In some embodiments, Label 1 (L1) is the label associated with A-LISPs at the base interrogation position; Label 2 (L2) is the label associated with C-LISPs at the base interrogation position; Label 3 (L3) is the label associated with G-LISPs at the base interrogation position; and Label 4 (L4) is the label associated with T-LISPs at the base interrogation position. The base interrogation position is the $1^{st}$ base from the 3' terminus of 5'-LISPs and the $1^{st}$ base from the 5' terminus of 3'-LISPs in the $1^{st}$ ligation cycle, shown as 251 in FIG. 4. The base interrogation position is the $2^{nd}$ base from the 3' terminus of 5'-LISPs and the $2^{nd}$ base from the 5' terminus of 3'-LISPs in the $2^{nd}$ ligation cycle, shown as 252 in FIG. 4. Similarly, the base interrogation position is the $3^{rd}$ base from the 3' terminus of 5'-LISPs and the $3^{rd}$ base from the 5' terminus of 3'-LISPs in the $3^{rd}$ ligation cycle, shown as 253 in FIG. 4. Other decoding schemes can be designed following the spirit of this invention.

In some embodiments, the four detection labels comprise four different fluorescent dyes whose absorption and emission spectra are compatible with the detection devices. Many fluorescent dye labels are known in the art and commercially available. One of the factors to be considered in choosing these fluorescent dyes is that they should have minimal fluorescence energy transfer between them, since LISPs are ligated close together on the target molecule amplicons on magnetic microparticles. Because a pair of bases are interrogated in each ligation cycle of the paired-probe ligation, every color combination of labels represents a combination of two bases in the IS tag sequence.

However, since the color combination can not determine the sequence of these two bases, the base sequences of AC and CA will generate the same detection signals. Table 1 shown in FIG. 5*a* summarizes the color combinations and corresponding base pair combinations, assuming bases A, C, G, T are labeled with L1, L2, L3 and L4 in both 5'-LISP and 3'-LISP. The color codes can then be represented by ID codes for user friendliness. In the coding scheme of Table 1, there are total 10 distinguishable label combinations, including 4 unique base pair combinations, shown in Table 2 in FIG. 5*b*; and there 6 equivalent base combinations, shown in Table 3 in FIG. 5*b*. Therefore, each pair of bases in the IS tag can provide 10 ID codes. If the IS tag length is 6 bases as in FIG. 6, the theoretical number of available ID codes are 10×10×10=1,000. The ID code of an IS tag can be identified once the base composition is determined.

In some embodiments, short IS tags, such as 4 bases in length, are used. There are only two base interrogation positions in each LISP. The construct and design principles are the same as described above in FIG. 4. Better ligation specificity can be achieved by the LISPs due to the fact that these base interrogation positions are closer to the ligation site. Only two cycles of paired-probe ligation is required for elucidating 4-base IS tags. However, the available color codes from these LISPs become smaller, totaling 10×10=100 ID codes in theory for the analysis.

Figure 6:
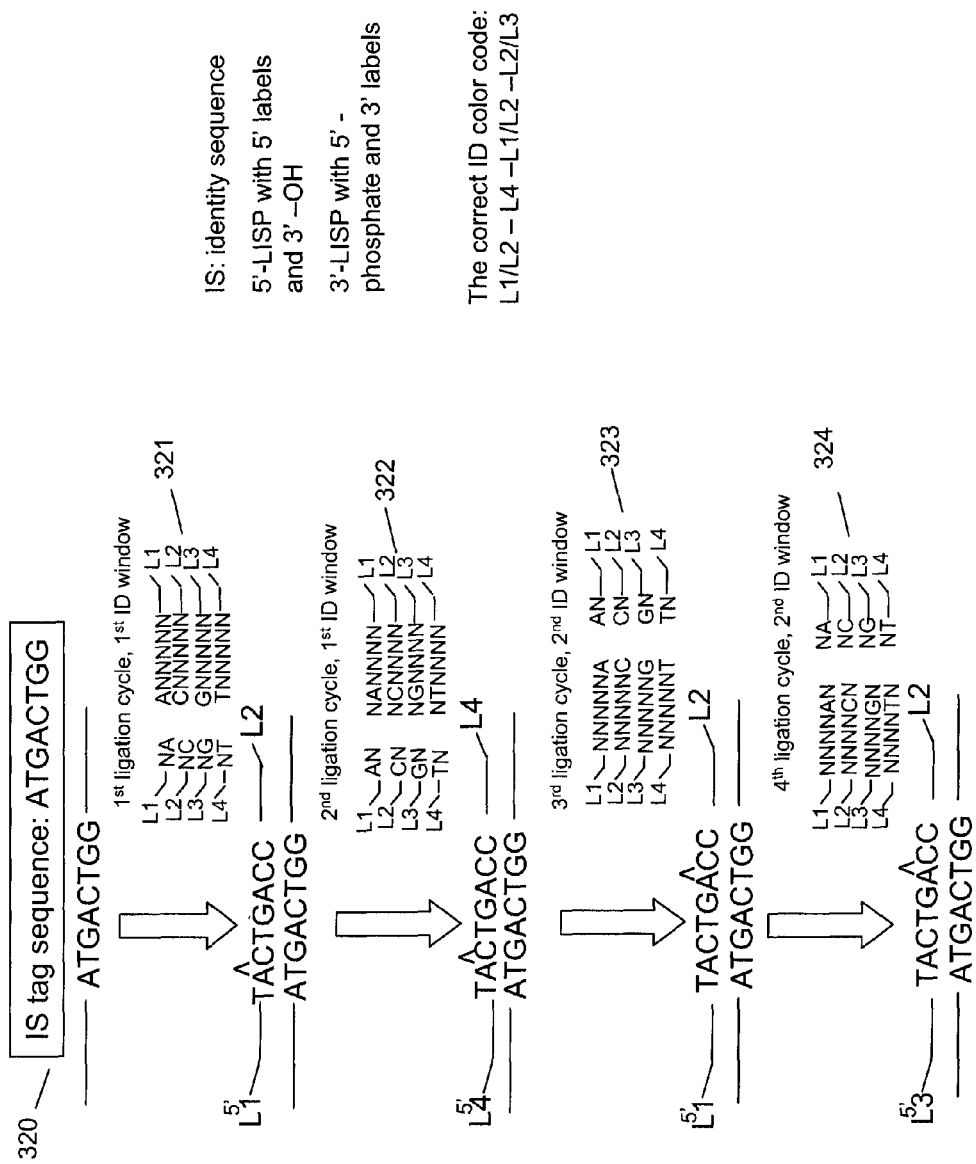
FIG. 6 depicts the principle of shifting ID window for sequential paired-probe ligation.

In other embodiments, longer IS tags are incorporated in order to increase the number of available ID codes, with shifting asymmetric 5'-LISP and 3'-LISP probe sets. An example is depicted in FIG. 6. In this case, 320 is an 8-base IS tag embedded in the template molecule. The $1^{st}$ ID window refers to four bases on the 5' end of IS tag 320 that are the subject of base interrogation by the $1^{st}$ and $2^{nd}$ cycles of ligation with LISPs 321 and 322. The $2^{nd}$ ID window refers to the other four bases on the 3' end of IS tag 320 that are the subject of base interrogation by the $3^{rd}$ and $4^{th}$ cycles of ligation with LISPs 323 and 324. These LISPs are asymmetrical because of the need for ID window shifting between the ligation cycles to maintain ligation specificity. LISPs 321, 322, 323, and 324 function by the same aforementioned principles when interrogating the four base compositions of respective ID windows, as illustrated in FIG. 6. However, only one pair of LISPs can be ligated on a specific IS tag. The available ID codes from the exemplary 8-base IS tag can be 10×10×10×10=10,000, which can be determined in just 4 cycles of ligation in the disclosed invention.

The IS tag design scheme illustrated in FIG. 6 provides a larger number of available ID codes while maintaining better ligation specificity, presumably due to better base discrimination at the ligation site. Other similar schemes can be designed following the spirit of this invention.

E. Target Sequence Analysis

Determination of IS tags provides gene or locus specific identity of those target sequences at nucleic acid amplicon clusters. Further sequence specific analysis can be carried out on these amplicons immobilized on the surface to obtain sequence variations, including, but not limited to, mutation, SNP, or methylation, of specific genes of interest, using nucleic acid analysis methods known in the art, including, but not limited to, labeled probe ligation, single-base extension, DNA sequencing, or melting curve analysis.

F. Apparatus for Multiplex Nucleic Acid Analysis

In a further aspect, the present invention provide a system for multiplex nucleic acid analysis.

In some embodiments, the system comprises a removable flow cell comprising a first reaction surface wherein biological reactions is implemented, and a second surface comprising a detection window through which the biological reactions inside said removable flow cell is detected. In some embodiments, the removable flow cell is capable of being separated from said temperature control unit to minimize the effect of said magnetic field on said first reaction surface of said removable flow cell during when necessary.

In some embodiments, the system comprises a plurality of removable flow cells.

In some embodiments, the system comprises a temperature control unit comprising a heat conducting layer and associated heating and cooling elements attached onto the heat conducting layer, and a magnetic unit that applies a magnetic field through said heat conducting layer, and optionally a thermal isolation layer in between the heat conducting layer and the magnetic unit, wherein the removable flow cell is located on the heat conducting layer for temperature regulation of the first reaction surface and is affected by the magnetic field afforded by the magnetic unit. The temperature regulation is performed by thermal electric coolers, resistive heaters together with cooling fans, or circulation of heated and cooled water. In some embodiments, the magnetic unit comprises a permanent magnet.

A variety of materials can be used for the thermal conducting plate, such as aluminum and copper. In general, the contact between the flow-cell and the thermal conducting plate needs to be tight enough to ensure good thermal transfer.

In some embodiments, the system comprises a fluidic control unit connected to said removable flow cell and controls reagent delivery to, and removal from, said removable flow cell.

In some embodiments, the system comprises a detection unit for detecting the presence and determining the position of appropriate labels on said first surface of the removable flow cell. In some embodiments, the detection unit comprises optics and a detector for fluorescence detection through the detection window of said removable flow cell.

In some embodiments, the system comprises an electronic control unit for controlling and coordinating modules of said system, and performing data analysis.

Figure 7:
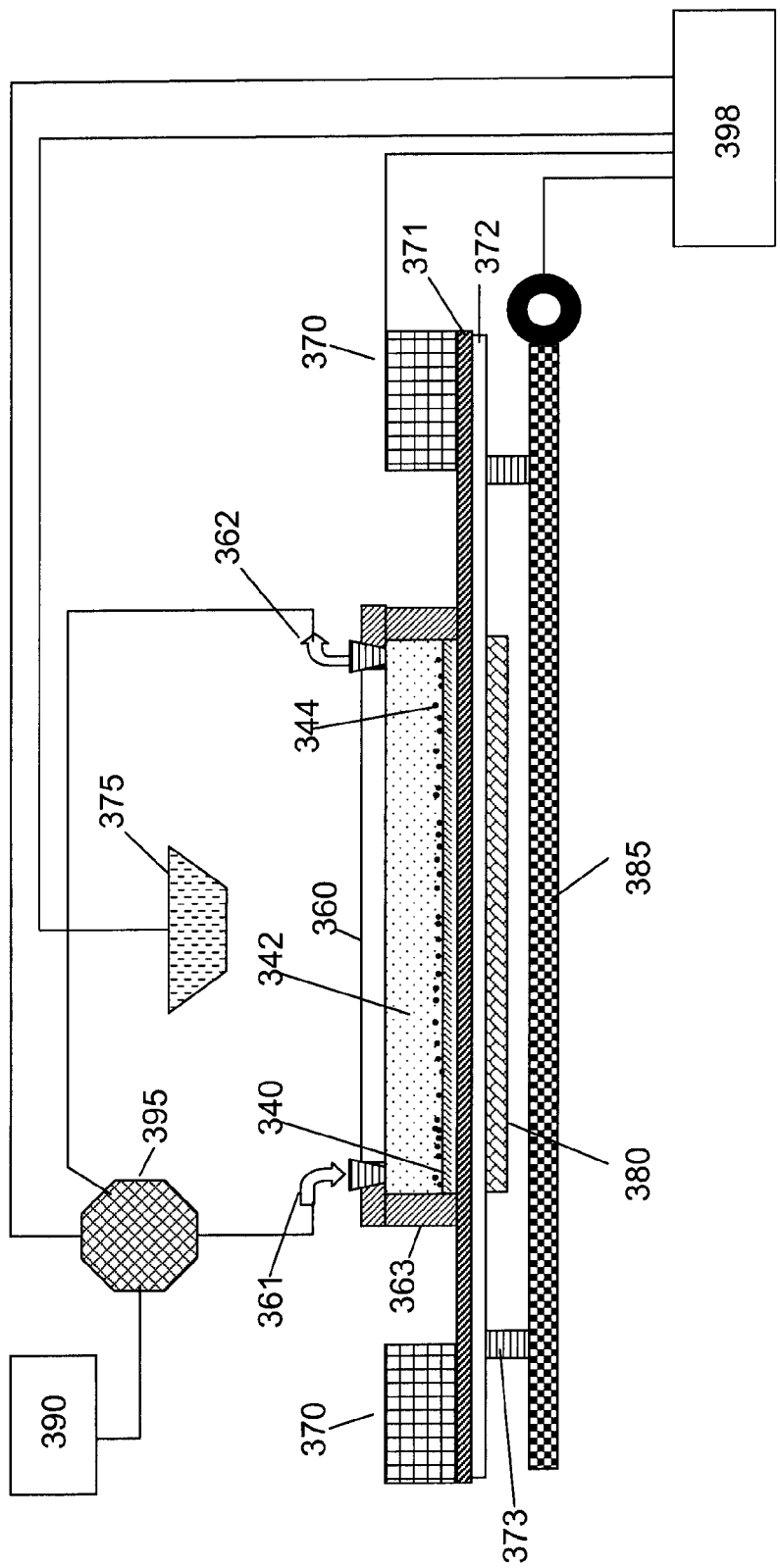
FIG. 7 illustrates an example of the system.

In some embodiments, a system for implementing this invention is illustrated in FIG. 7. The flow-cell 363 and its components 340, 342, 343, 345, 360, 361, and 362 are previously described in FIG. 2. The flow-cell is placed on a thermal conducting plate 371 that has one or optionally two thermal electric heating and cooling units 370 attached for regulating the temperature of the reaction surface inside the flow-cell. A thermal isolation layer 372 is optionally placed between the thermal conducting plate 371 and a permanent magnet 380 that is aligned with the reaction surface in the flow-cell. The whole assembly is mounted on an x-y precision moving stage 385 that can accommodate the scan area of the detection window in the flow-cell. A fluidic system 395 is connected to reagent unit 390 where all necessary reagents for the assay are stored, and optionally kept at specified temperature. The fluidic systems control the delivery and removal of reagents from the inlet and outlet of the flow-cell, as well as waste control. A detection unit 375 is mounted directly facing the detection window of the flow-cell, and is capable of automatically maintaining the focus and detecting all the optical labels used in the assay. Methods of fluorescence imaging are well known in the art. An example is a fluorescence microscope with filter cubes for different excitation and emission spectra. The Detection unit comprises a CCD imaging camera. All the control and data processing are handled by a computing unit 398.

In some embodiments, more than one flow-cell can be mounted on the system described above to maximize the efficiency of the system and provide sample flexibility. On such systems, different flow-cells can be programmed to run different assays. For example, sequential ligation chemistry might be running in one of the flow-cells, while fluorescence imaging might be on processed in another flow-cell on the system. More than one fluidic control unit or detection unit can be included as well.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

Example 1

Multiplex Genetic Testing for Early Cancer Detection

It is widely accepted that cancer is caused by accumulation of genetic changes of oncogenes, tumor-suppressor genes, and stability genes, including mutation and methylation of these genes. So far, many genetic changes have been identified as cancer biomarkers. It is evident from past cancer biomarker research that a better method of cancer detection is simultaneously testing a panel of genes that are involved in a particular cancer, instead of just a single gene. This invention provides a useful tool to detect low abundance biomarkers in a large background in highly multiplexed assays.

Early Detection of Colorectal Cancer

Colorectal cancer (CRC) is the third leading cause of cancer-related deaths in the United States when men and women are considered separately, and the second leading cause when both sexes are combined. American Cancer Society (ACS) recommends routine screenings starting at aged 50. CRC is highly curable if detected early. Non-invasive testing is a very important tool to promote routine screening of patients in order to detect cancers early and save lives.

Figure 8:
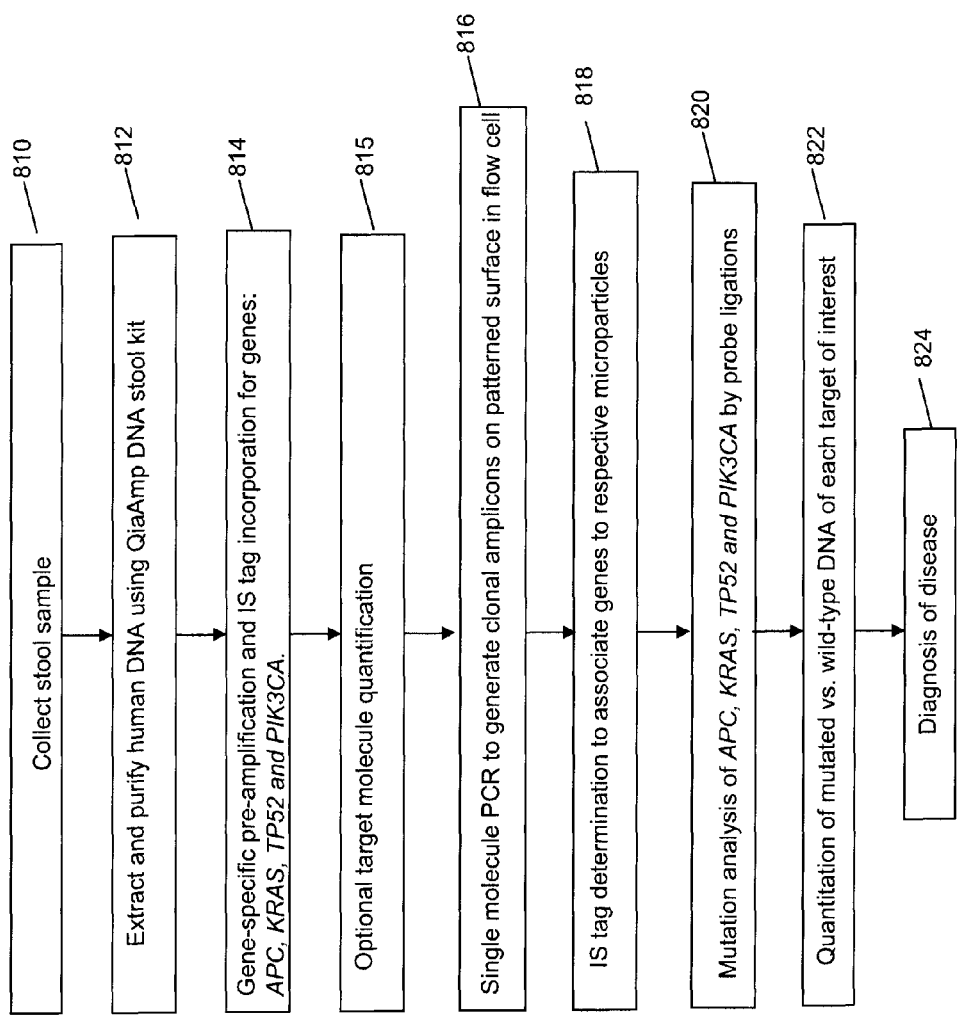
FIG. 8 illustrates an example of the use of multiplex nucleic acid analysis for non-invasive early detection of cancer.

A recent comprehensive study of genome-wide analysis of breast and colorectal genes revealed a set of 69 genes involved in colorectal cancer, with an average number of cancer genes in an individual colorectal cancer being 9, c.f. Sjoblom et al., "The Consensus Coding Sequences of Human Breast and Colorectal Cancers", 2006, 314, pp. 268-274. The great majority of the somatic mutations found in the study are single base mutations. Such mutated DNA can be quantified with respect to the wild-type DNA in the sample by the methods of this invention. An example is shown in FIG. 8. The major steps are described as follows.

(1) Stool DNA sample preparation, 810 and 812 in FIG. 8: Human DNA can be extracted from stool samples using QiaAmp DNA Stool Kit (Qiagene, Calif.) according to procedures outlined in QiaAmp DNA Stool Handbook. The majority of DNA fragments from this sample preparation are expected to be smaller than 200 bp in size.

(2) Gene-specific pre-amplification and IS tag incorporation 814: A fraction of the purified human DNA fragments from step 812 is used for gene-specific pre-amplification with a set of 18 primers containing universal primer sequences and unique IS tag sequences, which generates 18 amplicons flanked by universal primers that cover all 33 mutations in target genes (APC(20), TP53(5), KRAS(4), and PIK3CA(4) with the number of mutations indicated in parentheses), c.f. Diel et al. Gastroenterology, 2008, 135: 489-498, which is herein incorporated by reference. Each IS tag is assigned to a specific gene of interest, i.e. there are 18 IS tags (ID1 to ID18) in this assay. The assignment of IS tag to genes of interest is shown in Table A1. This is performed on a PCR thermal cycler.

(3) Optionally, in step 815, the amplicons from the pre-amplifications 814 is quantified by real-time PCR to determine the dilution factor of template molecules for the next step.

(4) Single molecule nucleic acid amplification on patterned slide in step 816: template molecules from the above pre-amplifications, together with other reagents, including magnetic microparticles with one of the universal primers attached, are distributed over a hydrophilic/hydrophobic patterned slide mounted in a removable flow cell as described previously to generate individual reaction droplets on the surface. There is less than one copy of the template molecule on average in each reaction droplet. The reaction droplets are covered with mineral oil and thermal cycled for nucleic acid amplification on the system. The PCR reagents are removed from the removable flow cell, and the slide with magnetic microparticles retained on the surface by magnetic field is washed with buffers. A fraction of the microparticles on the slide will have nucleic acid amplicons of a single template molecule.

(5) IS tag determination 818: All IS tags embedded in the amplicons on the microparticles are determined by sequential paired-probe ligation chemistry disclosed in this invention. Each microparticle is assigned to a particular gene of interest via the pre-determined IS tag identity (ID). However, there might be more than one mutation in some of the genes. When a unique ID cannot be determined for a specific microparticle, it is excluded from further analysis.

Figure 9:
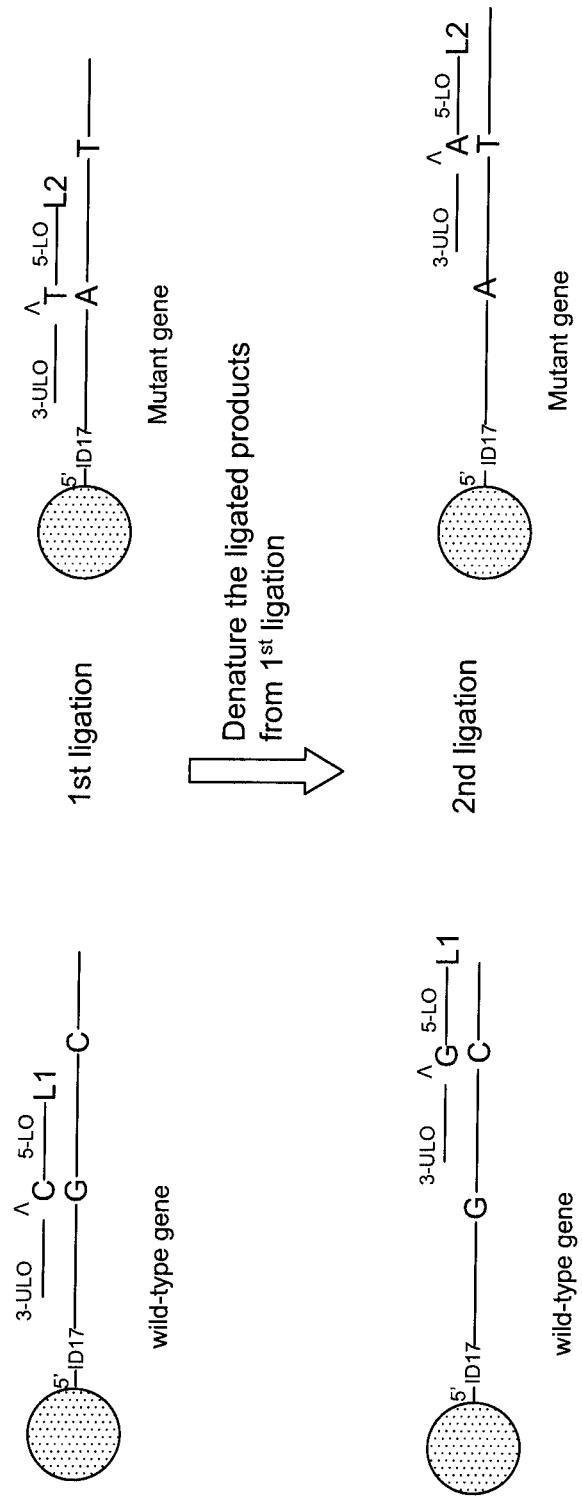
FIG. 9 depicts an exemplary embodiment of the present invention.

(6) Mutation analysis on magnetic microparticles 820: 33 mutations of colorectal cancer genes can be assessed by probe ligations. Two or more labels can be used to differentiate wild-type and mutant genes. However, they can be of the same label set for all the genes under testing, since the mutation analysis occurs on separated magnetic microparticles whose associations to specific genes are already determined in step 5 above. In FIG. 9, L1 and L2 are for wild-type and mutant targets respectively. Unligated oligonucleotides are washed away from the slide at elevated temperature before imaging. The labels reveal the mutation variations of these genes. When there is more than one mutation on amplicons of a specific gene, multiple cycles of ligation can be carried out on the same microparticle for different mutation sites. For example, shown in FIG. 9, the amplicon ID17 from Exon 7 of TP53 has two single base mutations (Table A1). The $1^{st}$ and $2^{nd}$ probe ligations determine the respective mutation variations of them on the same microparticles.

(7) Mutation analysis is quantified in 822 by compared the mutant to wild-type genes in the sample.

(8) Possible diagnosis of cancer can be determined in 824 by trained professionals if disease correlation is known.

TABLE A1

Mutated genes for colorectal cancer detection*

| IS tag | Gene | Amplicon | Mutation |
|---|---|---|---|
| ID1 | APC | APC-1 | single base mutation |
| ID2 | APC | APC-2 | deletion |
| ID2 | APC | APC-2 | deletion |
| ID3 | APC | APC-3 | single base mutation |
| ID3 | APC | APC-3 | deletion |
| ID3 | APC | APC-3 | single base mutation |
| ID4 | APC | APC-4 | insertion |
| ID4 | APC | APC-4 | single base mutation |
| ID4 | APC | APC-4 | single base mutation |
| ID5 | APC | APC-5 | single base mutation |
| ID5 | APC | APC-5 | deletion |
| ID6 | APC | APC-6 | deletion |
| ID7 | APC | APC-7 | single base mutation |
| ID7 | APC | APC-7 | deletion |
| ID8 | APC | APC-8 | single base mutation |
| ID9 | APC | APC-9 | deletion |
| ID10 | APC | APC-10 | deletion |
| ID10 | APC | APC-10 | deletion |
| ID10 | APC | APC-10 | deletion |
| ID11 | APC | APC-11 | insertion |
| ID12 | KRAS | KRAS | single base mutation |
| ID12 | KRAS | KRAS | single base mutation |
| ID12 | KRAS | KRAS | single base mutation |
| ID12 | KRAS | KRAS | single base mutation |
| ID13 | PIK3CA | PIK3CA Exon 9 | single base mutation |
| ID13 | PIK3CA | PIK3CA Exon 9 | single base mutation |
| ID14 | PIK3CA | PIK3CA Exon 20-1 | single base mutation |
| ID15 | PIK3CA | PIK3CA Exon 20-2 | single base mutation |
| ID16 | TP53 | TP53 Exon 5 | single base mutation |
| ID17 | TP53 | TP53 Exon 7 | single base mutation |
| ID17 | TP53 | TP53 Exon 7 | single base mutation |
| ID18 | TP53 | TP53 Exon 8 | single base mutation |
| ID18 | TP53 | TP53 Exon 8 | single base mutation |

*Gastroenterology 2008, 135: 489-498.

Example 2

Quantitative Multiplex Nucleic Acid Analysis

Quantitative analysis of 20 single base mutations on genomic DNA as follows.

Step 1. Target encoding 20 template molecules of the target sequences on genomic DNA are prepared by gene specific preamplification using 4-base IS tags (ID1 to ID20) embedded primers, c.f. FIG. 1c. Asymmetric PCR is used in the preamplification to generate single strand template molecules that simplifies the nucleic acid amplification.

Step 2. Nucleic acid amplification The prepared template molecules from step 1 are then circularized on extension oligonucleotides and nucleic acid amplified by rolling circle amplification on 20 types of magnetic microparticles. The extension oligonucleotides on a magnetic microparticle contain a specific anti-IS tag sequence that ensures only one target sequence is specifically ligated and amplified on a given magnetic microparticle in this assay. The RCA is carried out isothermally by $\phi$29 polymerase in solution. The ratio of magnetic microparticles and template amount is optimized to achieve no more than one template molecule per microparticle. Positive microparticles are identified by a dye labeled universal primer sequence that confirms the existence of amplified products on the microparticles.

Step 3. Sequential paired-probe ligation for IS tag identification The magnetic microparticle obtained in step 2 are randomly distributed into a flow-cell on the system as illustrated in FIG. 7 to determine IDs of each magnetic microparticle on the surface using 2 cycles of paired-probe ligation for the 4-base IS tags. Thorough wash of magnetic microparticles with wash buffer between the ligation cycles are necessary.

Step 4. Target sequence analysis and quantitation Subsequent multiplex assay for all 20 mutations on the microparticles is conducted using single base extension method with labeled dNTPs. Image analysis identifies all the 20 mutations on the positive magnetic microparticles.

Quantitation of each mutated or wild-type target sequence is achieved by counting the number of positive magnetic microparticles of each mutated or wild-type sequence.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of identifying target nucleic acid sequences in a sample, comprising:
   (a) generating from a sample a plurality of first template molecules and a plurality of second template molecules, wherein said first template molecules comprise a sequence of a first target nucleic acid and a first identity sequence (IS) tag, and said second template molecules comprise a sequence of a second target nucleic acid and a second IS tag, and wherein said first IS tag comprises a first identification (ID) code and said second IS tag comprises a second ID code;
   (b) generating at least one cluster of nucleic acid amplicons by nucleic acid amplification of said first template molecules and at least one cluster of nucleic acid amplicons by clonal amplification of said second template molecules in parallel individual reactions on a surface, wherein said clusters of nucleic acid amplicons are spatially separated; and
   (c) identifying said ID codes of said IS tags of said nucleic acid amplicons on said surface to determine the target nucleic acid sequences represented by said nucleic acid amplicons and the step (c) of identifying said ID codes of said IS tags of said nucleic acid amplicons further comprises:
   (c-1) hybridizing a pair of labeled IS probes (LISPs) from a pool of LISPs with said clusters of nucleic acid amplicons, thereby said pair of LISPs are juxtaposed, wherein each said LISP comprises: (i) a sequence complimentary to the IS tag sequence it hybridizes to, and (ii) a detectable label associated with a designated base at base interrogation positions, and wherein there are two sets of the LISPs in each pool of LISPs, with one set being the 3' labeled IS probes (3'-LISPs) that comprise 5' phosphate groups and 3' detectable labels, and the other set being the 5' labeled IS probes (5'-LISPs) that comprise 5' detectable labels and 3' hydroxyl groups;
   (c-2) performing a paired-probe ligation of said pair of juxtaposed LISPs;
   (c-3) detecting the presence of said detectable labels on said ligated pair of LISPs on said IS tags of said nucleic acid amplicons, and elucidating the base composition at said base interrogation positions of said IS tags according to the detectable label combination of said ligated pair of LISPs, wherein two specified base positions on IS tags and one on each side of said paired probes are interrogated;
   (c-4) denaturing said ligated pair of LISPs from said analyte molecule;
   (c-5) repeating steps (c-1) to (c-4) until all bases of base interrogation positions in said IS tags are interrogated without duplication and all base composition of said IS tags are elucidated; and
   (c-6) determining the ID codes of said IS tags on said nucleic acid amplicons by comparing said base composition to designated ID codes, wherein $10^n$ (or $10^n$) kinds of the base combinations are distinguished in n times of the paired-probe ligation.

2. The method of claim 1, wherein the position of each cluster of nucleic acid amplicons is kept fixed relative to other clusters on the surface during said nucleic acid sequence analysis.

3. The method of claim 1, further comprising determining the sequence variations of said target nucleic acid sequences by analyzing the sequence variations of said clusters of said nucleic acid amplicons on said surface.

4. The method of claim 1, wherein said first and second target nucleic acid sequences can be the same or different; and there can be more than said first and second target nucleic acid sequences.

5. The method of claim 1, further comprising quantifying the number of clusters of nucleic acid amplicons from said template molecules to infer the amount of each target nucleic acid sequence in said sample.

6. The method of claim 1, wherein said spatially separated clusters of nucleic acid amplicons are generated on said surface through enzymatic amplification or replication, and at least one of the primers used in said amplification or replication is attached to said surface during said nucleic acid amplification.

7. The method of claim 1, wherein each said cluster of nucleic acid amplicons is generated on a solid support on said surface through enzymatic amplification or replication, and at least one of the primers used in said amplification or replication is attached to said solid support on said surface during said nucleic acid amplification.

8. The method of claim 1, wherein said parallel individual reactions are carried out in a plurality of individual aqueous droplets on a surface, wherein each droplet comprises reagents for nucleic acid amplification or replication, including a plurality of primers.

9. The method of claim 8, wherein said individual aqueous droplets are formed by water-in-oil emulsion on said surface, and an oil phase of said water-in-oil emulsion comprises a water immiscible liquid.

10. The method of claim 8, wherein said nucleic acid amplification or replication of template molecules is carried out in hydrophilic reaction sites surrounded by a hydrophobic surface, wherein each hydrophilic reaction site comprises a said individual aqueous droplet.

11. The method of claim 8, wherein said DNA amplification is polymerase chain reaction (PCR), and said surface is thermal cycled during said nucleic acid amplification.

12. The method of claim 8, wherein said nucleic acid amplification or replication is carried out through circularization of single stranded template molecules and subsequent isothermal rolling circle amplification by a DNA polymerase, on extension oligonucleotides attached at 5' ends on said surface, and said extension oligonucleotides are complementary at 3' ends to the circularized template molecules and comprise free 3' —OH groups for enzymatic extension.

13. The method of claim 8, wherein some of the said individual aqueous droplets further comprise at least one microparticle comprising at least one of said primers attached on surface.

14. The method of claim 13, wherein nucleic acid amplicons are generated on the surface of magnetic microparticles; and said magnetic microparticles are immobilized on said surface by a physical force or by a chemical linkage.

15. The method of claim 1, wherein there are four different detectable labels on the two sets of the LISPs with each detectable label representing a designated base (A, C, G, T) at base interrogation positions, and wherein all probes needed for all possible base combinations at said base interrogation positions are included in each pool of LISPs.

16. The method of claim 1, wherein a different pool of LISPs is used in each ligation cycle, and wherein different base positions on said IS tags are sequentially interrogated in each ligation cycle.

17. The method of claim 1, wherein the labels on said LISP comprises fluorescent dyes, electrochemical labels, or nanoparticles.

\* \* \* \* \*